(12) United States Patent
Lee et al.

(10) Patent No.: US 7,867,747 B2
(45) Date of Patent: Jan. 11, 2011

(54) FIBRINOLYTIC METALLOPROTEASE AND COMPOSITION COMPRISING THE SAME

(75) Inventors: Sang-Hyeon Lee, Busan (KR); Dong-Geun Lee, Busan (KR); Jeong-Ho Jeon, Incheon (KR); Nam-Young Kim, Busan (KR); Jung-Hyun Lee, Gyeonggi-do (KR); Sang-Jin Kim, Seoul (KR); Min-Kyung Jang, Busan (KR)

(73) Assignee: Korea Ocean Research and Development Institute, Kyunggido (KR)

( * ) Notice: Subject to any disclaimer, the term of this patent is extended or adjusted under 35 U.S.C. 154(b) by 225 days.

(21) Appl. No.: 12/097,892

(22) PCT Filed: Nov. 8, 2006

(86) PCT No.: PCT/KR2006/004666

§ 371 (c)(1),
(2), (4) Date: Jun. 18, 2008

(87) PCT Pub. No.: WO2008/056840

PCT Pub. Date: May 15, 2008

(65) Prior Publication Data

US 2009/0317890 A1 Dec. 24, 2009

(30) Foreign Application Priority Data

Nov. 8, 2006 (KR) .................. 10-2006-0109824

(51) Int. Cl.
*C12N 9/50* (2006.01)
*C12N 15/57* (2006.01)
*C12N 15/70* (2006.01)
*A61K 38/48* (2006.01)

(52) U.S. Cl. .................. 435/219; 435/69.1; 435/252.3; 435/252.31; 435/320.1; 424/94.67

(58) Field of Classification Search .................. None
See application file for complete search history.

(56) References Cited

U.S. PATENT DOCUMENTS 5,260,060 A 11/1993 Markland, Jr. et al.
6,440,414 B1 8/2002 Kendrick et al.
6,825,025 B2 11/2004 Wei et al.
7,642,079 B2 * 1/2010 Cayouette et al. ........... 435/212

FOREIGN PATENT DOCUMENTS

KR 10 2007 0011667 1/2007

OTHER PUBLICATIONS

Moncrief, J. S., et al., 1995, The enterotoxin of *Bacteroides fragilis* is a metalloprotease, Infection and Immunity, 63(1): pp. 175-181.*
Selistre de Araujo, H. S., et al., 1995, Molecular cloning and sequence analysis of cDNAs for metalloproteinases from broad-banded copperhead *Agkistrodon contortrix laticinctus*, Archives of Biochemistry and Biophysics, 320(1): pp. 141-148.*
Siigur, E., et al., 1996, "cDNA cloning and deduced amino acid sequence of fibrinolytic enzyme (lebetase) from *Vipera lebetina* snake venom", Biochemical and Biophysical Research Communications, 224(1): pp. 229-236.*
Xiao-Yan, D., et al., 1998, "Purification, cDNA cloning and molecular characteristic of a fibrinolytic enzyme from the venom of *Agkistrodon acutus*", Journal of Natural Toxins, 7(2): pp. 159-172.*
Rodrigues, V. M., et al., 2000, "Structural and Functional Characterization of Neuwiedase, a Nonhemorrhagic Fibrin(ogen)olytic Metalloprotease from *Bothrops neuwiedi* Snake Venom", Archives of Biochemistry and Biophysics, 381(2): pp. 213-224.*
Francischetti, I. M. B., et al., 2003, "Cloning of a salivary gland metalloprotease and characterization of gelatinase and fibrin(ogen)lytic activities in the saliva of the Lyme disease tick vector *Ixodes scapularis*", Biochemical and Biophysical Research Communications, 305(4): pp. 869-875.*
Jeong, Y.-K., et al., 2004, "Molecular cloning and characterization of the gene encoding a fibrinolytic enzyme from *Bacillus subtilis* Strain A1", World Journal of Microbiology & Biotechnology, 20(7): pp. 711-717.*
Siigur, J., et al., 2005, "*Vipera lebetina* Venom Contains All Types of Snake Venom Metalloproteases", Pathophysiology of Haemostasis and Thrombosis, 34(4-5): pp. 209-214.*

* cited by examiner

*Primary Examiner*—Nashaat T Nashed
*Assistant Examiner*—William W Moore
(74) *Attorney, Agent, or Firm*—Gifford, Krass, Sprinkle, Anderson & Citkowski, P.C.

(57) ABSTRACT

The present invention relates to a novel protease, a polynucleotide encoding the protease, and a fibrinolytic agent comprising the same. The protease is obtained from a new gene source by using metagenomic library technology, and can replace the conventional fibrinolytic agent.

13 Claims, 10 Drawing Sheets

FIG. 1A

```
GTCCGAACGCCGCTCTCGGCTGCTCGGTCTCCGAGTGACGGC         -491
GCCTGAGAGGGCGCTGGTGCGCTCTCCTGCCGCCGATTCTTCCTTCTGTTCGCGC        -421
TACGGGAGAAGCCCTTTGGCAATTCTATTCCGCCGCTGTCCTCCTGGCCCGGCAAAAT     -351
GATTCCACTCATGTGAACATCTTCTTCTTTCAACGTTTATCAAGTGAGCAAATAGTAATTTAAATAC  -281
AGTTTAACCGAACCATTGTACCGTAAAACGGTGGACCTCAAAATTATTACCCATCCACAACTGCAATATC  -211
TTTCGTTTGCCAGAATGGAGGGTTAATTCGGCATTGACCTTGTTAACCTGCGGTTATAATTTTGTTG    -141
ACTTTCGTGACGTCTATGCAATCACCGTCCCGTAGTAAGCGTTGTACCCCGCCTGCAATAGCGCTAAA    -71
GCGCAGACCACGACGGTATTGTTGTCGAAGCCCAAGTGAACCACTACTTTGGATCGCAAAGGAGAAACC    -1
ATGGAACCAGAACCGATCAAAACCTGCACCGTGCTCGAGAATCCCGGCTATCAGCCTATACACGCACCGA   +70
 M  E  P  E  P  I  K  T  C  T  V  L  E  N  P  G  Y  Q  P  I  H  A  P
NcoI                                XhoI
CAGATGTTTCACCCCAACCTGCTCTGCGGCGAAGCAGTCCCCGTGCCAACACCGCCAACTGT          +140
 Q  M  F  H  P  N  L  L  C  G  E  A  V  P  V  P  T  P  P  T  V        +47
TGATGCGGTCGGTCATGCTCTTCCGCAAGAACATGGCGCAAGATACGTGTCCACTTTATGGACGGC      +210
 D  V  S  P  Q  P  V  L  A  A  M  E  A  V  P  V  P  T  P  P  T  V     +70
CGATGCGGTCGGTCATGCTCTTCCGCAAGAACATGGCGCAAGATACGTGTCCACTTTATGGACGGC      +210
 D  A  V  M  L  F  R  K  K  W  R  D  G  K  I  L  R  V  H  F  M  D  G  +70
GACCCGGATGTGCACCGCAAAGTGGAGGAAGTGGCTCACACCTGGAGCCCATGCCAATGTTCGCTTCA    +280
 D  P  D  V  H  R  K  V  E  E  V  A  H  T  W  S  R  H  A  N  V  R  F  +93
AGTTCGTCGACGATCCAGCGGCGGATATCCGCATTTCGTTTACGCAACCGGGATCCTGGTCTTATCTGGG +350
BamHI
 K  F  V  D  D  P  A  A  D  I  R  I  S  F  T  Q  P  G  S  W  S  Y  L  G +117
```

FIG. 1B

```
AACGGATGCGCTTCGGATTGCCAGTCCCAATCGACGATGAATTTTGGCTGGTTGACGCCGCGCTCTCCA    +420
 T  D  A  L  R  I  A  R  S  Q  S  T  M  N  F  G  W  L  T  P  R  S  P    +140
GACAGCGAGTATAACCGAGTGTTATTCACGGAATTTGGGCTCGGCCTTGTGCATGAACATCAAA          +490
 D  S  E  Y  N  R  V  V  I  H  E  F  G  H  A  L  G  L  V  H  E  H  Q     +163
ATCCCGACAACGGCATTCCGTGGAACAAACCGGCGGTCTACGAATATTATAGTGGCCCCAACAACTG      +560
 N  P  D  N  G  I  P  W  N  K  P  A  V  Y  E  Y  Y  S  G  P  P  N  W     +187
GTCCAAAGAACAGGTTGACACCAATCTGTTCCAACAATATTCAGAAGACCAGGTTCCGTTTCACGGCTTC   +630
 S  K  E  Q  V  D  T  N  L  F  Q  Q  Y  S  E  D  Q  V  R  F  T  G  F     +210
GATCGCGAATCAATCATGCTCTACGATGACAAGGAGTTCATTGGCCGAATGTATCCTAAAGCCGCCAACGAGTTGAT  +700
 D  R  E  S  I  M  L  Y  D  D  K  E  F  I  G  R  M  Y  P  K  A  N  E  L  I    +233
ACAGAGATCTCTCGGCTGATGACAAGGAGTTCATTGGCCGAATGTATCCTAAAGCCGCCAACGAGTTGAT   +770
 N  R  D  L  S  A  D  D  K  E  F  I  G  R  M  Y  P  K  A  N  E  L  I     +257
CGTCGATGATCCACCCCCGCCAGTCCGAAATCAGCAGATATGGCGAAATCGACACCTATACATTTCTGGTC  +840
 V  D  D  P  P  R  A  S  E  I  S  R  Y  G  E  I  D  T  Y  T  F  L  V     +280
ACCCAAAAAGGATCCTACCCGCATTGAAACCGACGGCCGGACCGACCTGGTGATGCTGCTATACGGGCCGG +910
 T  Q  K  G  S  Y  R  I  E  T  D  G  R  T  D  L  V  M  L  L  Y  G  P     +303
          BamHI
AAGATGATGCAAATCGATCGCCGGTCGCGGTGATAGTGGTCGCCGGTATCACTGAAGA              +980
 E  D  D  T  K  L  I  A  A  D  D  D  S  G  R  R  L  N  P  R  I  T  E  E  +327
ACTGGGATTGGGGCAATACACGGTTGCAGTGCGTTTGCAGATTTCAGCAACGCCAGTAAATACGCCGTT   +1050
 L  D  W  G  K  Y  T  V  R  L  Q  H  F  S  Q  R  Q  T  G  K  Y  A  V     +350
GGCGTCTATAGGGATGACGCGGCGGAGTAAGGCGCCCCAGAATAGAAAGTCACCGATCAACTCCCCGGG   +1120
 G  V  Y  R  D  D  A  A  E  *                                             +359
                                                        SmaI
CACAGGCCACAGGTTACGCCATTGAGTAGGGCGCCGGGGAGTTCAATTCCGGGGCG                +1190
GCCTTACGCAAATCGCATGATACAATGTAACACCCTTGACCACAAAGTGCATCCAACCTGTATGAAATCAT +1260
GTTCGCAACGGTATGCAGACCAGGGTTGAGGAAATGATCGAAAATGATCGAAAACATATTTAAGGCTTCGGTAAACACTA +1330
```

FIG. 1C

```
CATCCACCACCACTTCCATTACCGGCGTTCTCCCGCGATCGCGGGCGCGTGAGTCATGGTCTACTTTGAA   +1400
ATTGGGGATTATCCTGGGCGCGCTCAGTCTATTGCTTTTCCTTTCGGGGCATGTGGAGGTTCTTCTGCA   +1470
                                                                PstI
GCCGCGCCAAGCGGTGAAGCGATTGCCTTTGAAGAGATGCCCGAAGGCATGGGCCGCGGCTACCCCAACG   +1540
TTTCATTGGCCAATATCAATAACAACGGCACTGGCCCTTGAGAACGGAGATCGGGCTCCTGGCTTCAACCT   +1610
                                                              SacII
GCAGTTGAGGATGGCGCCTACATTAATCTCGACGACCTGAAGGGTCGGCCGGTTATGCTCAATTTCTGG   +1680
PstI
GCAACGTGGTCCGCCCTGCCGGAAGAAATGCCCGACATTATCAAAGCCTATGAAGCGGACGATGAGT   +1750
TGGTGGTGCTGGCCCGTTAACGTCGCGCGGTGAATCCGTTTACAGAAGATTTCCAGAT   +1820
TTCCATGCCGGTGTTGCTGGACCCCAAACGCTGAGCTGTCCGAGCTCTTCGGCGTGCTTGGCATGC   +1885
                                           SacI                 SphI
```

US 7,867,747 B2

FIBRINOLYTIC METALLOPROTEASE AND COMPOSITION COMPRISING THE SAME

CROSS-REFERENCE TO RELATED APPLICATIONS

This application is the U.S. national phase of PCT/KR2006/004666 filed Nov. 8, 2006, which claims priority of Korean Patent Application KR 10-2006-0109824 filed Nov. 8, 2006.

BIOLOGICAL DEPOSIT INFORMATION

Vector designation pES63H9pro3-MIC was deposited on Sep. 17, 2010, under the Budapest Treaty with Korean Culture Center of Microorganisms with accession number KCCM11100P; and vector designation pES63H9pro3-ES63H9-MIC was deposited on Sep. 17, 2010, under the Budapest Treaty with Korean Culture Center of Microorganisms with accession number KCCM11101P. These deposits will be made available to the public for the enforceable term of this patent.

FIELD OF THE INVENTION

The present invention relates to a novel metalloprotease, a polynucleotide encoding the metalloprotease, and a fibrinolytic composition comprising the same. The invention provides a metalloprotease derived from a new gene source by using the metagenomic library technology, and a fibrinolytic agent that can substitute for a previous fibrinolytic agent.

BACKGROUND OF THE INVENTION

Proteases are indispensable constituents of all forms of life including bacteria, and are of major importance in the food, leather, detergent, pharmaceutical, and waste management industries, and in the diagnosis of illness. The amount of proteases used constitutes two-thirds of the total amount of enzymes used in various industries, which is expected to increase.

In addition, a number of proteases involved in blood homeostasis have been purified and characterized from various sources. Some of these proteases are fibrinolytic enzymes that are capable of digesting fibrin. At present, the fibrinolytic agents available for clinical use are mostly plasminogen activators such as a tissue-type plasminogen activator, a urokinase-type plasminogen activator, and a bacterial plasminogen activator streptokinase.

Fibrinolytic enzymes have been purified from fermented food, earthworms (Nakajima N. et al., *Biosci. Biotechnol. Biochem.* Vol. 57, pp 1726-1730, 1993), and mushrooms (Kim J. H. et al., *Biosci. Biotechnol. Biochem.* Vol. 65, pp 356-362, 2001) as well as snake venom (Leonardi A. et al., *Toxicon.* Vol. 40, pp 55-62, 2002). These enzymes, which consist of both serine proteases and metalloproteases, have been suggested as potential sources of oral fibrinolytic drugs. Recently, fibrinolytic enzymes in shark cartilage extract have been characterized. These fibrinolytic activities have correlated with the presence of two proteases in the extract, which were inhibited by 1,10-phenantroline, indicating that the enzymes were metalloproteases (Ratel D. et al., *Thromb. Res.* Vol. 1115, pp 143-152, 2005).

sPA, uPA, tPA, APSAC, and the like, which are the fibrinolytic agents used for clinical use, can act as a plasminogen activator being capable of producing plasmin to digest fibrin. Such agents disadvantageously show a low specificity to the fibrin, and cause undesired side effects. For example, sPA causes pyrexia, low blood pressure, and allergies. uPA causes bleeding and takes a long time to inject into subjects.

Consequently, the search continues for other fibrinolytic enzymes from various sources for use in thrombolytic therapy.

Screenings for novel enzymes, including proteases, have mainly used the cultivation-dependent approach. Many valuable enzymes originated from cultivable microorganisms; however, the rate of screening for novel enzymes is significantly decreased when standard cultivation methods are used owing to a high rediscovery frequency (Strohl W. R. et al., *Drug Discov. Today*, Vol. 5, pp 39-41, 2000). In order to use complex communities, efforts to overcome the problem of non-cultivability have been continuously made.

SUMMARY OF THE INVENTION

An object of the present invention is to provide a novel zinc-dependent metalloprotease obtained from the new gene source by using metagenomic library technology.

Another object of the present invention is to provide a nucleotide molecule encoding a protease having fibrinolytic activity, a vector including the nucleotide molecule, and a transformant introduced by the recombinant plasmid.

A further object of the present invention is to provide a promoter that is an original promoter of zinc-dependent metalloprotease, and an expression vector including the promoter.

To resolve the problem of a conventional fibrinolytic agent, the present invention is to provide a novel fibrinolytic agent that is derived from a non-cultivable microorganism, and that would possess better fibrinolytic activity than the conventional fibrinolytic agent.

The present invention provides a fibrinolytic Zn-dependent metalloprotease that has a molecular weight of about 39 kDa to 40 kDa, an optimum pH of 6 to 8, an optimum temperature of 40 to 60° C., a conserved amino acid sequence in an active site of the metalloprotease of His-Glu-Phe-Gly-His (SEQ ID NO:10), and in which the metalloprotease activity is inhibited by a metal chelating agents $Mg^{2+}$ or $Zn^{2+}$. Preferably, the protein includes an amino sequence as shown in SEQ ID NO:2, and more preferably a peptide encoded by a nucleotide sequence of SEQ ID NO:1.

In another embodiment, the present invention provides a polynucleotide molecule encoding the amino acid sequence as shown in SEQ ID NO:2, and more preferably a nucleotide sequence of SEQ ID NO:1.

In a further embodiment, the present invention provides a vector including the polynucleotide molecule and a transformant introduced by the recombinant plasmid. Preferably, the vector further includes a promoter that is connected to a 5'-end of the polynucleotide encoding zinc-dependent metalloprotease, and contains a 542 bp to 546 bp-sized DNA fragment including a nucleotide sequence of SEQ ID NO: 3. More preferably, the vector further includes a MxeIntein chitin binding domain (CBD) that is connected to a 3'-end of the polynucleotide encoding zinc-dependent metalloprotease and is derived from a DNA fragment located between NcoI and BamHI in pTXB3. Most preferably, the vector includes a nucleotide sequence as shown in SEQ ID NO: 8, and is illustrated as pES63H9pro3-ES63H9-MIC in FIG. 6a.

In a fourth embodiment, the present invention provides a promoter that is located in a 5' end of the polynucleotide encoding zinc-dependent metalloprotease having fibrinolytic activity, preferably a 542 bp to 546 bp-sized DNA fragment including a nucleotide sequence of SEQ ID NO: 3, and more preferably a nucleotide sequence of SEQ ID NO: 4.

In another embodiment, the present invention provides an expression vector including pUC, 542 bp to 546 bp-sized DNA fragment including a nucleotide sequence of SEQ ID NO: 3, and an 853 bp-sized MxeIntein chitin binding domain (CBD) that was a DNA fragment located between NcoI and BamHI in pTXB3. Most preferably, the expression vector is illustrated as pES63H9pro3-MIC in FIG. 5a.

In still another embodiment, the present invention provides a pharmaceutical composition comprising a zinc-dependent metalloprotease, and preferably a pharmaceutical composition used for a fibrinolytic agent.

BRIEF DESCRIPTION OF THE DRAWINGS

FIG. 1A to 1C are nucleotide sequences of a metalloprotease clone and deduced amino acid sequences of an enzyme. The nucleotide sequences show the nucleotide sequence of a protease gene, its flanking regions, the underlined conserved sequence in the active site of zinc-dependent metalloproteases, and some unique restriction sites according to the present invention.

In FIG. 2, lane M shows size marker, lane C shows cell-free extract, lane P shows purified enzyme by affinity chromatography, and the arrow indicates the position of protease.

DETAILED DESCRIPTION OF THE INVENTION

Figure 2:
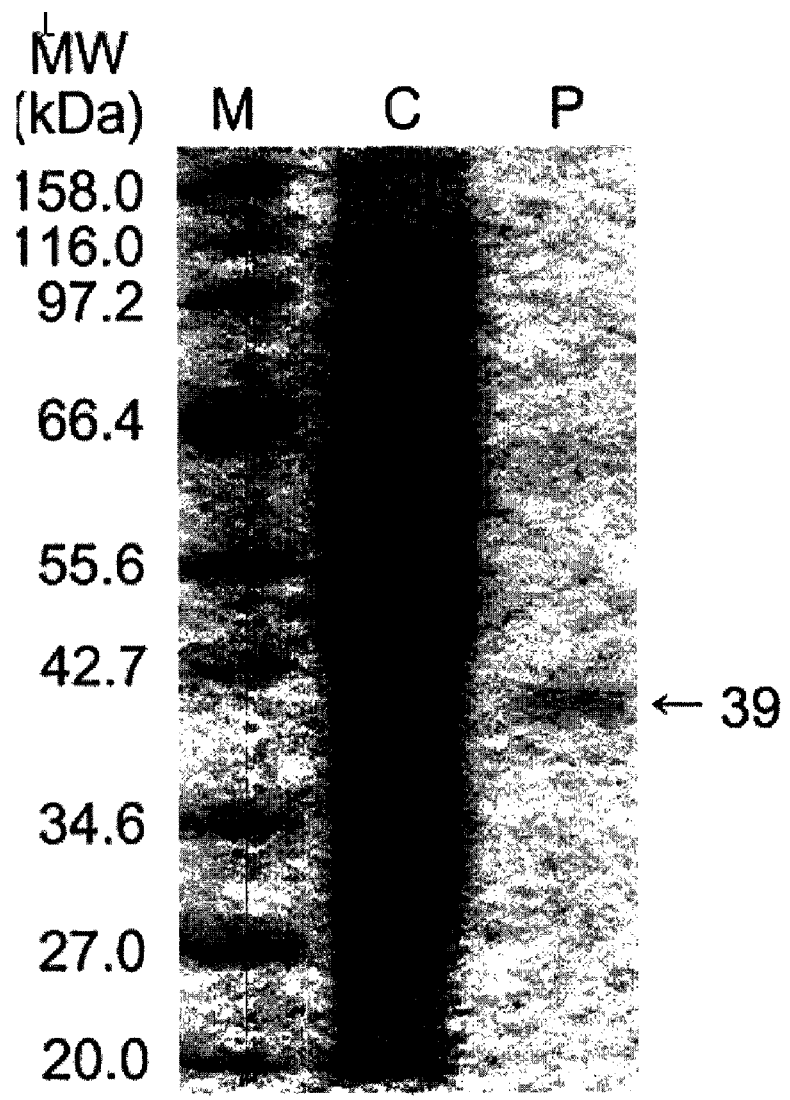
FIG. 2 is SDS-PAGE of protease from E. coli cells harbouring pES63H9pro3-ES63H9-MIC according to the present invention.

Before the present invention is disclosed and described, it should be understood that this invention is not limited to the particular configurations, process steps, and materials disclosed herein, and such configurations, process steps, and materials may be varied. It should also be understood that the terminology employed herein is used for the purpose of describing particular embodiments only and is not intended to limit the scope of the present invention, which will be limited only by the appended claims and equivalents thereof.

The protease of the present invention has a molecular weight of about 39 to 40 kDa, and preferably about 39,490 Da. Preferably, the protease contains 359 amino acid residues of SEQ ID NO:2, and more preferably a peptide encoded by a 1,080 bp-sized open reading frame of a nucleotide sequence as shown in SEQ ID NO:1.

The protease has an optimum pH of 6 to 8 and an optimum temperature of 40 to 60° C. and more preferably the purified enzyme shows optimal activity at about 50° C. and pH 7.0 for 1 hour.

The enzyme activity according to the present invention is inhibited by metal-chelating agents, such as EDTA, EGTA, and 1,10-phenantroline. The enzyme activity is enhanced by metal ions, such as $Co^{2+}$, $Ca^{2+}$, and $Ni^{2+}$, but inhibited by $Mg^{2+}$ and $Zn^{2+}$ ions. The enzyme activity of zinc-dependent carboxypeptidase is activated by $Co^{2+}$ ion (Lee S. H. et al., *Biosci. Biotech. Biochem.* Vol. 58, 1490-1495, 1994), but inhibited by a high concentration of $Zn^{2+}$ ions.

The enzyme hydrolyzes a fibrin, and can thus be used as a therapeutic agent to treat thrombosis.

His-Glu-X-X-His (SEQ ID NO:11), where X is any non-conserved amino acid, is the conserved sequence in the active-site of some zinc-dependent metalloprotease (Vallee B. L. et al., *Biochemistry* Vol. 29, pp 5647-5659, 1990). These findings suggest that the enzyme is a zinc-dependent endopeptidase and aminopeptidase.

The protease of present invention contains the conserved sequence of His-Glu-Phe-Gly-His at 150 to 154 amino acid residue, suggesting that it is a zinc-dependent metalloprotease (FIG. 1). The amino acid sequence of recombinant protease has highest similarity to neutral zinc dependent metalloprotease (accession no. CDD16541 at NCBI), which is a member of the peptidase family M12A requiring zinc for catalysis, and astacin of crayfish (accession no. CDD24541 at NCBI).

Bode et al. (Bode W. et al., *FEBS Let.* Vol. 331, 134-140, 1993) reported that astacins, metalloprotease, and snake venom exhibited identical zinc-binding environments (His-Glu-X-X-His-X-X-Gly-X-X-His (SEQ ID NO:12)), and this zinc-binding environment was also a conserved sequence in metalloprotease disintegrins, another member of the zinc-dependent metalloprotease superfamily (Poindexter K. et al., *Gene* Vol. 237, pp 61-70, 1999).

In addition, His-Glu-X-X-His-Ala-Leu-Gly-X-X-His-Glu (SEQ ID NO:13) sequence is a conserved sequence in zinc-dependent metallopeptidase family members (accession no. CDD16541 at NCBI), and this sequence is also found in the protease of the present invention.

The recombinant protease is produced by using pES63H9pro3-MIC as a vector and E. coli DH5α as a host. When the protease coding gene is cloned with its 0.5-kb upstream region (FIG. 1), the protease is constitutively expressed in E. coli cells without requiring induction materials, such as IPTG or mitomycin C (FIG. 2). This indicates that the cloned gene contains its own promoter that can be worked in E. coli cells. This result indicates that a positive clone, pES63H9 having catalytic activity, possesses a complete gene encoding a putative protease. The nucleotide sequence and deduced amino acid sequence shown in FIG. 1A to 1C are shown below.

```
         GTCCGAACGCCGCTCTGGCTGCTCGGTCTCCGAGTGACGGC                              -491

GCCTGAGAGGGCGCGCTGGTGCGCTCTTCCGGGATTGCCTCCTGCGCCGATTCTTCCTTCTGTTCGCGGC    -421

TACGGGAGAAGCCCTTTGGCAATTCTATTCCGCCGCTCTGCTGCGGATTGTCCTCCTGGCCCGGCAAAAT    -351

GATTCCACTCATGTGAACATCTTCTTTCTTTTCAACGTTTTATCAAGTGAGCAAATAGTAATTTAAATAC    -281
```

-continued

```
AGTTTAACCGAACCATTGTACCGTAAAACGGTGGACCTCAAAATTATTACCCATCCACAACTGCAATATC        -211

TTTCGTTTGCCAGAATGGAGGGTTAATTCGGCATTGACCTTACTGTTAACCTGCGGTTATAATTTTGTTG        -141

ACTTTCGTGACGTCTATGCAATCACCGTCCGTAGTAAGCGTTGTACCCGCCCGCCTGCAATAGCGCTAAA        -71

GCGCAGACCACGGACGGTATTGTTGTCGAAGCCCAAGTGAACCACTACTTTGGATCGCAAAGGAGAAACC        -1

ATGGAACCAGAACCGATCAAAACCTGCACCGTGCTCGAGAATCCCGGCTATCAGCCTATACACGCACCGA        +70
NcoI                            XhoI
  M  E  P  E  P  I  K  T  C  T  V  L  E  N  P  G  Y  Q  P  I  H  A  P         +23

CAGATGTTTCACCCCAACCTGTGCTTGCGGCGATGGAAGCAGTCCCCGTGCCAACACCGCCGCCAACTGT        +140
  T  D  V  S  P  Q  P  V  L  A  A  M  E  A  V  P  V  P  T  P  P  P  T  V     +47

CGATGCGGTCATGCTCTTCCGCAAGAAGTGGCGCGATGGCAAGATACTGCGTGTCCACTTTATGGACGGC        +210
   D  A  V  M  L  F  R  K  K  W  R  D  G  K  I  L  R  V  H  F  M  D  G        +70

GACCCGGATGTGCACCGCAAAGTGGAGGAAGTGGCTCACACCTGGAGCCGCCATGCCAATGTTCGCTTCA        +280
  D  P  D  V  H  R  K  V  E  E  V  A  H  T  W  S  R  H  A  N  V  R  F        +93

AGTTCGTCGACGATCCAGCGGCGGATATCCGCATTTCGTTTACGCAACCGGGATCCTGGTCTTATCTGGG        +350
                                              BamHI
 K  F  V  D  D  P  A  A  D  I  R  I  S  F  T  Q  P  G  S  W  S  Y  L  G      +117

AACGGATGCGCTTCGGATTGCCAGGTCCCAATCGACGATGAATTTTGGCTGGTTGACGCCGCGCTCTCCA        +420
   T  D  A  L  R  I  A  R  S  Q  S  T  M  N  F  G  W  L  T  P  R  S  P       +140

GACAGCGAGTATAACCGAGTGGTTATTCACGAATTTGGGCACGCGCTCGGCCTTGTGCATGAACATCAAA        +490
  D  S  E  Y  N  R  V  V  I  H  E  F  G  H  A  L  G  L  V  H  E  H  Q       +163

ATCCCGACAACGGCATTCCGTGGAACAAACCGGCGGTCTACGAATATTATAGTGGCCCGCCCAACAACTG        +560
 N  P  D  N  G  I  P  W  N  K  P  A  V  Y  E  Y  Y  S  G  P  P  N  N  W     +187

GTCCAAAGAACAGGTTGACACCAATCTGTTCCAACAATATTCAGAAGACCAGGTCCGTTTCACCGGCTTC        +630
   S  K  E  Q  V  D  T  N  L  F  Q  Q  Y  S  E  D  Q  V  R  F  T  G  F      +210

GATCGCGAATCAATCATGCTCTACCCAATCCCGAATGAGTTCACTGTAGGTGATTTCGAAGTTGGTTGGA        +700
  D  R  E  S  I  M  L  Y  P  I  P  N  E  F  T  V  G  D  F  E  V  G  W       +233

ACAGAGATCTCTCGGCTGATGACAAGGAGTTCATTGGCCGGATGTACCCCAAGCCGGCCAACGAGTTGAT        +770
 N  R  D  L  S  A  D  D  K  E  F  I  G  R  M  Y  P  K  P  A  N  E  L  I     +257

CGTCGATGATCCACCCCGCGCGTCCGAAATCAGCAGATATGGCGAAATCGACACCTATACATTTCTGGTC        +840
   V  D  D  P  P  R  A  S  E  I  S  R  Y  G  E  I  D  T  Y  T  F  L  V      +280

ACCCAAAAAGGATCCTACCGCATTGAAACCGACGGCCGGACGGACCTGGTGATGCTGCTATACGGGCCGG        +910
         BamHI
 T  Q  K  G  S  Y  R  I  E  T  D  G  R  T  D  L  V  M  L  L  Y  G  P        +303

AAGATGACACCAAACTGATCGCCGCCGATGATGATAGTGGTCGCCGTCTGAACCCGCGTATCACTGAAGA        +980
  E  D  D  T  K  L  I  A  A  D  D  D  S  G  R  R  L  N  P  R  I  T  E  E    +327

ACTGGATTGGGGCAAATACACGGTGCGTTTGCAGCATTTCAGCCAACGCCAGACCGGTAAATACGCCGTT       +1050
   L  D  W  G  K  Y  T  V  R  L  Q  H  F  S  Q  R  Q  T  G  K  Y  A  V      +350

GGCGTCTATAGGGATGACGCGGCGGAGTAAGGCGCTCCCAGAATAGAAAGTCACCGATCAACTCCCCGGG       +1120
 G  V  Y  R  D  D  A  A  E  *                                   SmaI       +359

CACAGGCCACAGGTTACGCCATTGAGTAGGGCGCCTTTGACCCATGCCGGGGAGTTCAATTCCGGGGGCG       +1190

GCCTTACAGCAAATCGCATGATACAATGTAACCCTTGACCACAAAGTGCATCCAACCTGTATGAAATCAT       +1260

GTTCGCAACGGTATGCAGACCAGGGTTGAGGAAATGATCGAAAACATATTTAAGGCTTCGGTAAACACTA       +1330
```

-continued

```
CATCCACCACCACTTCCATTACCGCGTTCTCCCGCGATCGCGGCGCGTCGAGTCATGGTCTACTTTTGAA  +1400

ATTGGCGATTATCCTGGGCGCGCTCAGTCTATTGCTTTTCCTTTTCGGGGCATGTGGAGGTTCTTCTGCA  +1470
                                                                 PstI

GCCGCGCCAAGCGGTGAAGCGATTGCCTTTGAAGAGATGCCCGAAGGCATGGGCCGCGGCTACCCCAACG  +1540
                                                       SacII

TTTCATTGGCCAATATCAATAACAACGGCACTGGCCTTGAGAACGGAGATCGGGCTCCTGGCTTCAACCT  +1610

GCAGTTGGAGGATGGCGCCTACATTAATCTCGACGACCTGAAGGGTCGGCCGGTTATGCTCAATTTCTGG  +1680
PstI

GCAACGTGGTGTCCGCCCTGCCGGGAAGAAATGCCCGACATTATCAAAGCCTATGAAGCGGACGATGAGT  +1750

TGGTGGTGCTGGCCGTTAACGTGCGCGAAGAGATCGGCGCGGTGAATCCGTTTACAGAAGATTTCCAGAT  +1820

TTCCATGCCGGTGTTGCTGGACCCAAACGCTGAGCTGTCCGAGCTCTTCGGCGTGCTTGGCATGC       +1885
                                        SacI              SphI
```

The protease of the present invention can be defined by biochemical characteristics or amino acid sequence. The fibrinolytic protease contains an amino acid sequence as shown in SEQ ID NO:2, and an amino acid sequence that is substantially identical to the amino acid sequence. The substantial identity means an amino acid sequence having at least 98% amino acid sequence homology obtained after aligning the amino acid sequence of the present invention with another amino acid sequence and analyzing the aligned amino acid sequence with a sequence analysis program.

In accordance with an embodiment of the present invention, the present invention provides a nucleotide molecule encoding the fibrinolytic protease.

As used herein, the term "polynucleotide molecule" means DNA (gDNA and cDNA) and RNA molecules as a whole, and the nucleotide constituting the polynucleotide can be natural nucleotide or its analogue which is modified at sugar or base. More preferably, the polynucleotide molecule includes a nucleotide sequence as shown in SEQ ID NO:1. The polynucleotide molecule encoding the fibrinolytic protease includes a polynucleotide that is substantially identical to the nucleotide sequence as shown in SEQ ID NO:1.

Metagenomes are genomes of non-cultivated microorganisms existing within a certain environmental microbial community. Hence, the generation and analysis of metagenomic libraries is a powerful approach to the collection and archiving of environmental genetic resources (Ferrer et al., Curr. Opin. Biotechno. Vol. 16, pp 588-593, 2005). Methods had been developed and used to overcome the non-cultivability of environmental microorganisms for biotechnology, namely cloning and the expression of metagenomes in suitable expression hosts.

In order to discover new proteases from metagenomic libraries, we screened a novel gene encoding enzyme having proteolytic activity from the constructed metagenomic library by direct cloning of environmental DNA of large DNA inserts.

In an embodiment of the present invention, the novel gene encoding a zinc-dependent proteolytic enzyme was picked up, sequenced, expressed in *E. coli* and characterized. A metagenomic library was constructed using total genomic DNA extracted from deep-sea clam beds of the west coast of Korea and a fosmid vector pCC1FOS in order to uncover novel gene sources.

In the screening course of the metagenomic library by the functional screening method, one clone from approximately 30,000 recombinant *Escherichia coli* clones showed proteolytic activity. The gene encoding the proteolytic enzyme was sub-cloned with a pUC19 vector and sequenced, and the result of homology research using a database of the gene revealed the protease to be a zinc-dependent metalloprotease. The cloned gene included the intact coding gene for a novel metalloproteinase and its own promoter.

In another embodiment of the present invention, the present invention provides a vector including the polynucleotide molecule encoding a zinc-dependent metalloprotease. The vector system can be constructed by using the general method in this art, and the specific preparation of the vector is described in Sambrook et al., *Molecular Cloning, A Laboratory Manual*, Cold Spring Harbor Laboratory Press, 2001, which is incorporated as a reference herein.

The vector of the present invention can be a typical cloning vector or an expression vector, and can be used for a prokaryotic host or a eukaryotic host. In consideration of the prokaryotic origin of the protease and manipulation convenience, the prokaryotic cell is preferred as a host. The present invention provides an *E. coli* vector including the polynucleotide molecule encoding zinc-dependent metalloprotease, for example the expression vector pES63H9pro-MIC. pES63H9pro-MIC includes a 546 bp-sized DNA fragment of SEQ ID NO:4, which is a DNA fragment located between EcoRI and NcoI in a promoter of the ES63H6 gene, and an 853 bp-sized MxeIntein chitin binding domain (CBD), which is a DNA fragment located between NcoI and BamHI in pTXB3.

In another embodiment, the present invention provides a transformant including the vector. Any host that is well-known for being stable and used for continuous cloning or expression can be used for the present invention, for examples *E. coli* JM109, *E. coli* BL21, *E. coli* RR1, *E. coli* LE392, *E. coli* B, *E. coli* X 1776, *E. coli* W3110, *Bacillus* sp. such as *B. substilis*, and *B. thuringiensis, Salmonella typhimurium, Serratia marcescens, Pseudomonas* sp, and the like.

The eukaryotic hosts are yeasts such as *Saccharomyces cerevisiae*, insect cell lines, human cell lines, and the like, for example the CHO cell line (Chinese hamster ovary), and W138, BHK, COS-7, 293, HepG2, 3T3, RIN, and MDCK cell lines.

The pharmaceutical composition of the present invention can be used as a fibrinolytic agent that causes fibrin clots to be degraded directly. Examples of treatable diseases include brain diseases such as cerebral thrombosis and cerebral embolism; pulmonary diseases such as pulmonary embolism and pulmonary infarction; peripheral nervous diseases such as deep vein thrombosis walking difficulty, anaemia caused by obstruction of blood flow, coronary artery necrosis, neuralgia, and hyperlipidemia; nephropathy, such as renovascular hypertension and renal insufficiency; and cardiac disorders such as angina pectoris, ischemic heart disease, and myocardial infarction, and the like.

The pharmaceutical composition can be formulated with pharmaceutically acceptable diluents. In general, the active agent can be mixed with diluents in liquid or solid form, and if necessary, can be formulated in a solid form such as tablet, granule, powder, spray, or capsule form, or in a liquid form such as emulsion, suspension, or general liquid form, with the addition of a solvent, dispersing agent, emulsifying agent, buffer, stabilizing agent, excipient, binding agent, dissolving agent, lubricant, and the like. The pharmaceutical composition of the present invention can be administered orally, paraenterally, or by a drop method. The diluents include starch, lactose, white sugar, mannitol, carboxymethylcellulose, corn starch, and inorganic salts for oral form. To formulate an oral dosage form, a surfactant, a fluidity-increasing agent, flavourful acids, a colorant, a flavouring agent, and the like are added to the formulation. For paraenteral dosage form, the active agent can be dissolved or suspended in distilled water, saline, a glucose solution, plant oils such as peanut oil, bean oil, corn oil, propylene glycol, or polyethylene glycol, and can have an anti-bacterial agent, stabilizing agent, isotonic agent, and analgesic agent added, if desired.

The pharmaceutical composition can be administered by an appropriate route depending on the formulation. The administration method does not limited particularly, and includes injection, oral administration and paraenteral administration. The paraenteral formulation can be administered intravenously, intramuscularly, or by subcutaneous injection. The dosage of the pharmaceutical composition can be determined depending on formulation, administration method, object of usage, and age, body weight, and condition of the subject to be administered. For example, the amount of active agent contained in the formulation is 10 μg-200 mg/kg per 1 day for an adult. However, a person skilled in the art can understand the change in the dosage in consideration of pharmacokinetics, administration method, and route; age, condition, and body weight of patient; characteristics and extent of disorder; and treatment frequency.

The present invention is further explained in more detail with reference to the following examples. These examples, however, should not be interpreted as limiting the scope of the present invention in any manner.

Example 1

Screening of the Protease Gene

*Escherichia coli* EPI300 (Epicentre, Madison, Wis., USA) as a host, and a fosmid, pCC1FOS (Epicentre) as a vector, were used in order to construct the metagenomic library of deep-sea sediment.

1-1: Isolation of the Sample DNA

A DNA library was constructed in a fosmid vector, pCC1FOS, using a sediment sample collected from a deep-sea clam bed community. This library was screened for proteolytic activity of the clones on a skim milk agar plate. As a result, a protease-positive clone, pES63H9, was selected.

Specifically, the sediment sample is a deep-sea sediment sample collected from a clam bed community in the deep-sea mud of the coast of Korea by Lee et al. (Lee et al., 2004, *J. Microbiol. Biotechnol.* Vol. 14, pp 906-913, 2004).

The DNA extraction method of Hurt et al. (Hurt, R. A., et al., *Appl. Environ. Microbiol.* Vol. 67, pp 4495-4503, 2001) was used for DNA isolation from deep-sea sediment samples with minor modifications, and further purification of the DNA was performed by direct extraction from agarose gel.

1-2: Metagenomic Library Construction

The metagenomic library was constructed according to the protocol of manufacture (Epicentre, Madison, USA).

Sheared and end-repaired DNA was ligated into pCC1FOS (Epicentre), and the ligated DNA was packaged using MaxPlax Lambda Packaging Extracts (Epicentre, Madison, USA). *E. coli* EPI300 (Epicentre) cells were infected using packaged DNA and plated on an LB agar medium supplemented with 12.5 μg chloramphenicol/ml and 1% skim milk for direct screening of protease activity.

1-3: Sub-Cloning and DNA Sequencing of the Protease Gene

The methods used for molecular cloning of the sample were based on Molecular Cloning: A Laboratory Manual ($2^{nd}$) written by Sambrook et al. (Sambrook E, Fritsch F, Maniatis T, Molecular Cloning: A Laboratory Manual, $2^{nd}$ ed., Cold Spring Harbor Laboratory, Cold Spring Harbor, N.Y., 1989). pUC19 was used as a vector for sub-cloning.

Specifically, Fosmid DNA was isolated from positive colonies and digested with EcoRI and SphI, and DNA fragments of 2 to 5-kb were ligated into the corresponding sites of pUC19. The ligated DNA was transformed into *E. coli* DH5α and the transformants were examined for proteolytic activity using LB agar medium supplemented with 100 μg ampicillin/ml and 1% skim milk.

Plasmid DNA (termed pUC-ES63H9) was isolated from a proteolytic clone and sequenced at Bionex Inc. (Seoul, Korea).

The nucleotide sequence of the protease of the present invention that was contained in pUC-ES63H9 2427 bp is shown in SEQ ID NO:5, and the gene construct included a protein coding sequence, its own promoter, and a 3' terminal sequence as represented in FIG. 5.

Sequence analysis of the gene was carried out using the DS Gene 1.5 program (Accelrys Inc., San Diego, Calif., USA).

Specifically, the nucleotide sequence analyzed by Bionex Inc. was further analyzed to determine the restriction sites, amino acid sequence, homology analysis, an active site, and the like by using a sequence analysis program. The analysis result is shown in FIG. 1.

FIG. 1 shows nucleotide sequences of the protease clone and deduced amino acid sequences of the enzyme. Specifically, FIG. 1 shows the nucleotide sequence of the protease gene, its flanking regions, the underlined conserved sequence in the active site of zinc-dependent metalloproteases, and some unique restriction sites. The deduced amino acid sequence of the gene product is indicated by the single letter codes under the nucleotide sequence.

As shown in FIG. 1, the gene is comprised of 1,080 bp with a G+C content of 54.5%, and the gene begins with ATG and ends with TAA. No typical Shine-Dalgarno or tandem inverted repeat sequences were found in the 5'- and 3'-non-coding regions, respectively. The gene encodes a protein of 359 amino acids with a molecular mass of 39,490 Daltons (Da) (FIG. 1). The amino acid sequence was 46% identical to metallopeptidase from *Dechloromonas aromatica* (accession no. AAZ45577 at NCBI).

By conserved domain searching (Marchler-Bauer, A. et al., *Nucleic Acids Res.* Vol. 33, pp D192-196, 2005), a His-Glu-X-X-His sequence (where X is any non-conserved amino acid) was found at positions 150 to 154 of the enzyme (FIG. 1). This is a conserved sequence in the active site of zinc-dependent metalloproteases. These findings suggest that the enzyme is a zinc-dependent metalloproteinase.

Example 2

Production of the Recombinant Protease

The pUC19 was used as the vector for construction of the expression plasmid and the *E. coli* DH5α (supE44, ΔlacU169 (φ80 lacZΔM15), hsdR17, recA1, EndA1, gyrA96, thi-1, relA1) was used as the host for manipulations and expression of the gene. The *E. coli* cells were routinely grown at 37° C. in Luria-Bertani (LB) broth (Difco, USA) and supplemented with 100 μg ampicillin/ml when required.

2-1: Construction of Expression Vector

The pUC-ES63H9 that was isolated in Example 1 was digested with EcoRI and BamHI, and a 0.9-kb DNA fragment of DNA fragments that were obtained by restriction digestion was ligated into the corresponding sites of pUC19, resulting in a pUC-ES63H9pro. The pTXB3 (New England Bio-labs Inc., Beverly, Mass., USA) was digested with NcoI and BamHI, and a 0.8-kb DNA fragment of DNA fragments that were obtained by restriction digestion was ligated into the corresponding sites of the pUC-ES63H9pro, resulting in an *E. coli* expression vector, pES63H9pro3-MIC (4.1 kb).

Figure 5A:
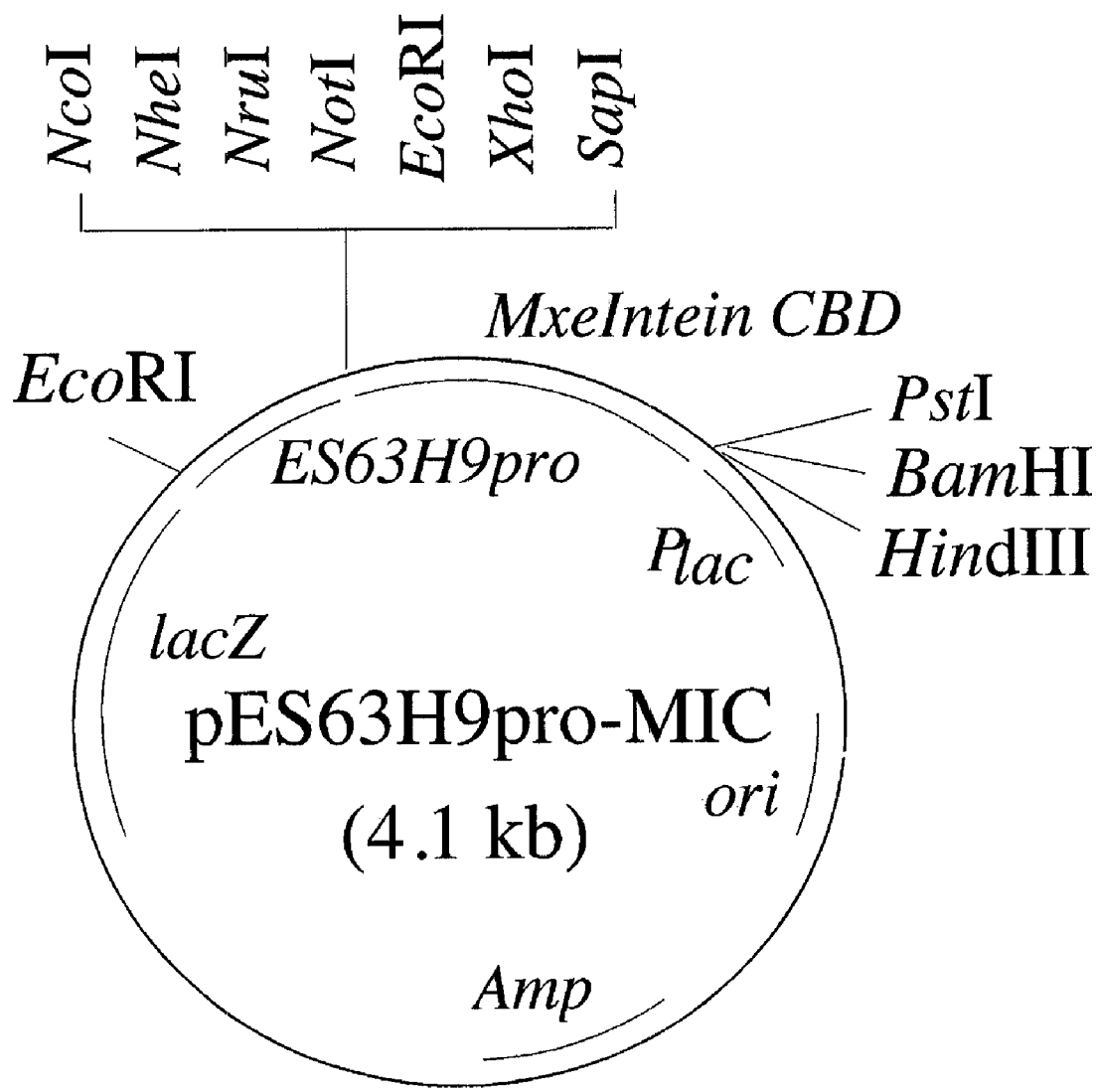
FIG. 5A and FIG. 5B show a preparation process and a cleavage map of pES63H9pro3-MIC (about 4.1 kb) in accordance with an embodiment of the present invention.
Figure 5B:
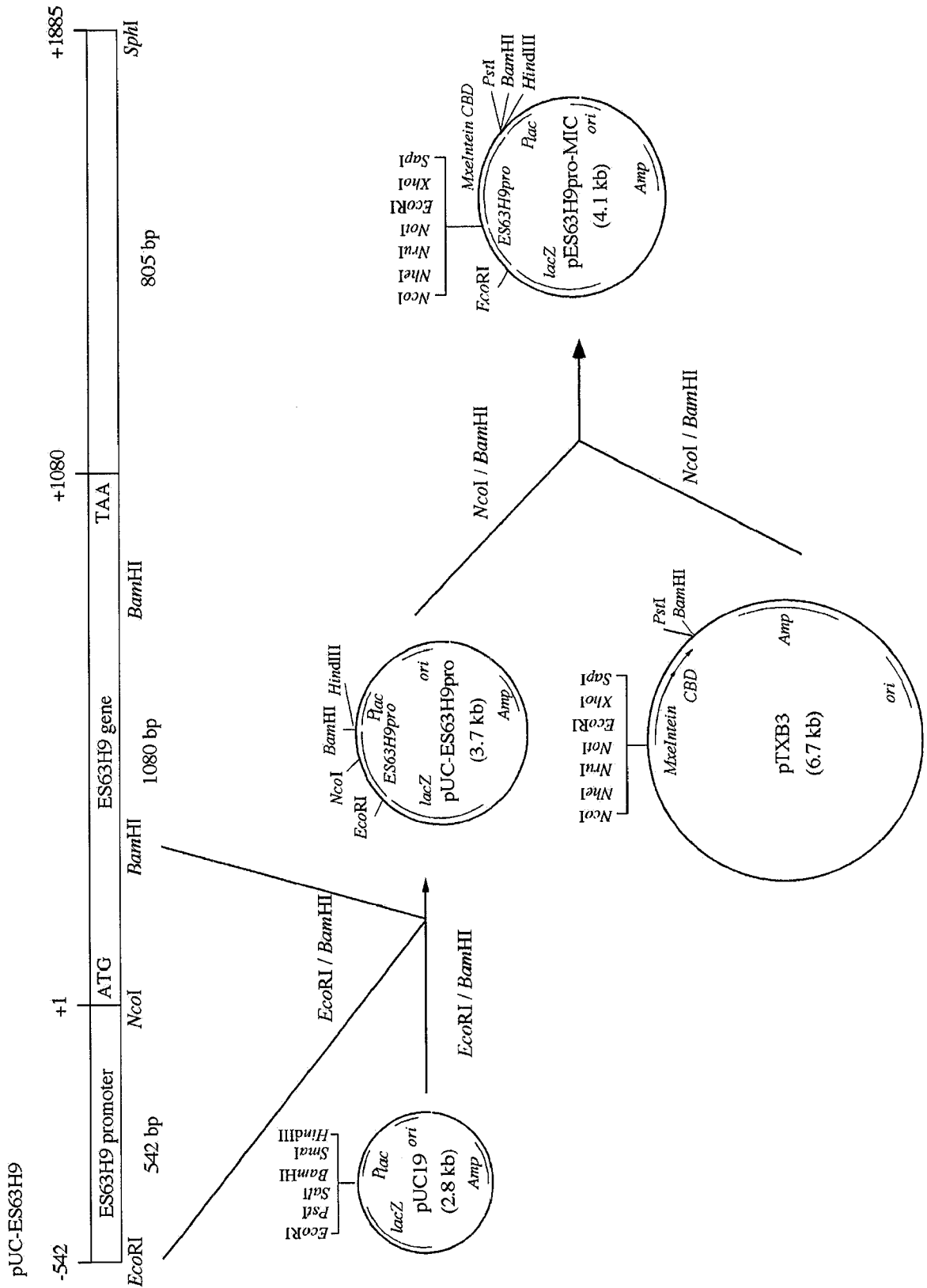

The preparation and cleavage map of the vectors are shown in FIG. 5A and FIG. 5B. The pES63H9pro3-MIC vector included a 546 bp-sized DNA fragment of SEQ ID NO:4 that was located between EcoRI and NcoI in a promoter of the ES63H6 gene, and an 853 bp-sized MxeIntein chitin binding domain (CBD) that was a DNA fragment located between NcoI and BamHI in pTXB3 for facilitating the affinity chromatography. The vector was deposited on Sep. 17, 2010, under the Budapest Treaty with Korean Culture Center of Microorganisms with accession number KCCM11100P. The MxeIntein chitin binding domain (CBD) was represented in SEQ ID NO:9, and the 546 bp-sized DNA fragment is shown in SEQ ID NO:4. The 546 bp-sized fragment included a 542 bp-sized fragment that was the original promoter of the protease, and a 6 nucleotide NcoI restriction site in its 5'-end in order to easily allow gene manipulation and cloning.

2-2: Expression of Recombinant Protease

The putative protease gene was amplified from the pUC-ES63H9 plasmid using Pyrobest DNA polymerase (Takara Bio Inc., Otsu, Japan) with a GeneAmp PCR System 2400 (PerkinElmer, Inc., USA).

The primers used were ES63H9_E2-F(5'-GAATTC-CATGGAACCAGAACCGATC-3') containing EcoRI and NcoI restriction sites (underlined) at the 5'-end and ES63H9_E1-R(5'-GCGGCCGCGCTCCGCCGCGTCATC-CCTATAG-3') containing a NotI restriction site (underlined) at the 5'-end.

```
Forward primer
                                    (SEQ ID NO; 6)
ES63H9_E2-F:  (5'-GAATTCCATGGAACCAGAACCGATC-3')

Reverse primer
                                    (SEQ ID NO; 7)
ES63H9_E1-R:  5'-GCGGCCGCGCTCCGCCGCGTCATCCCTATAG-3'
```

The amplified DNA was ligated to pGEM-T easy vector (Promega, Madison, USA), resulting in pGEMTe-ES63H9_E21. The pGEMTe-ES63H9_E21 carrying the putative protease gene was digested with NcoI and NotI, and a 1.1-kb DNA fragment of DNA fragments that were obtained by restriction digestion was ligated to the corresponding sites of the expression vector constructed in Example 2-1, pES63H9pro3-MIC, resulting in a recombinant plasmid. FIG. 5 shows the steps of constructing the recombinant plasmid and the cleavage map of the recombinant plasmid.

The recombinant plasmid was introduced into *E. coil* DH5α cells, which were then grown overnight, collected by centrifugation at 5,000×g for 5 min, and used for a recombinant plasmid preparation. The integrity of the recombinant plasmid was confirmed by restriction digestion using NcoI and NotT and the recombinant plasmid confirmed was designated pES63H9pro3-ES63H9-MIC (5.2 kb). The vector was deposited on Sep. 17, 2010, under the Budapest Treaty with Korean Culture Center of Microorganisms with accession number KCCM11101P.

Figure 6A:
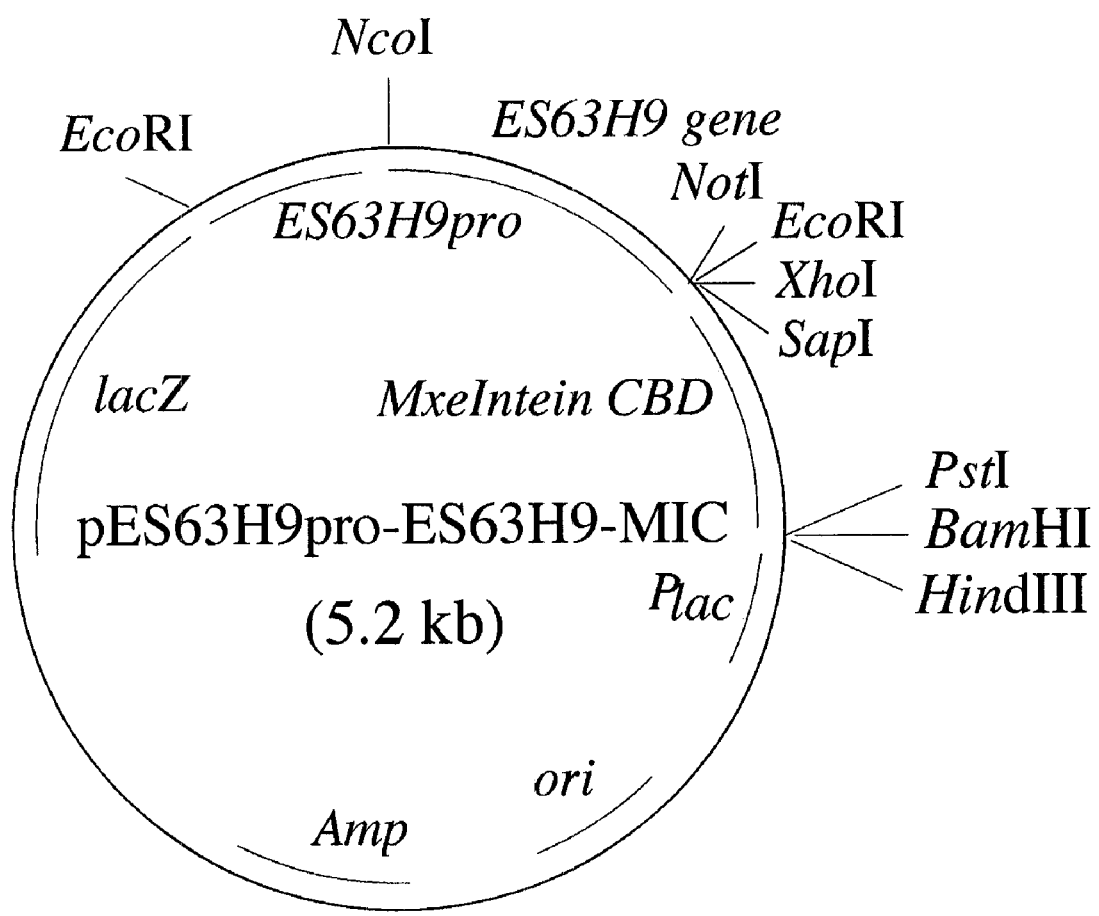
FIGS. 6A and 6B show the preparation and cleavage mpa of pES63H9pro3-ES63H9-MIC (5.2 kb) that includes a coding sequence of the present protease and promoter.
Figure 6B:
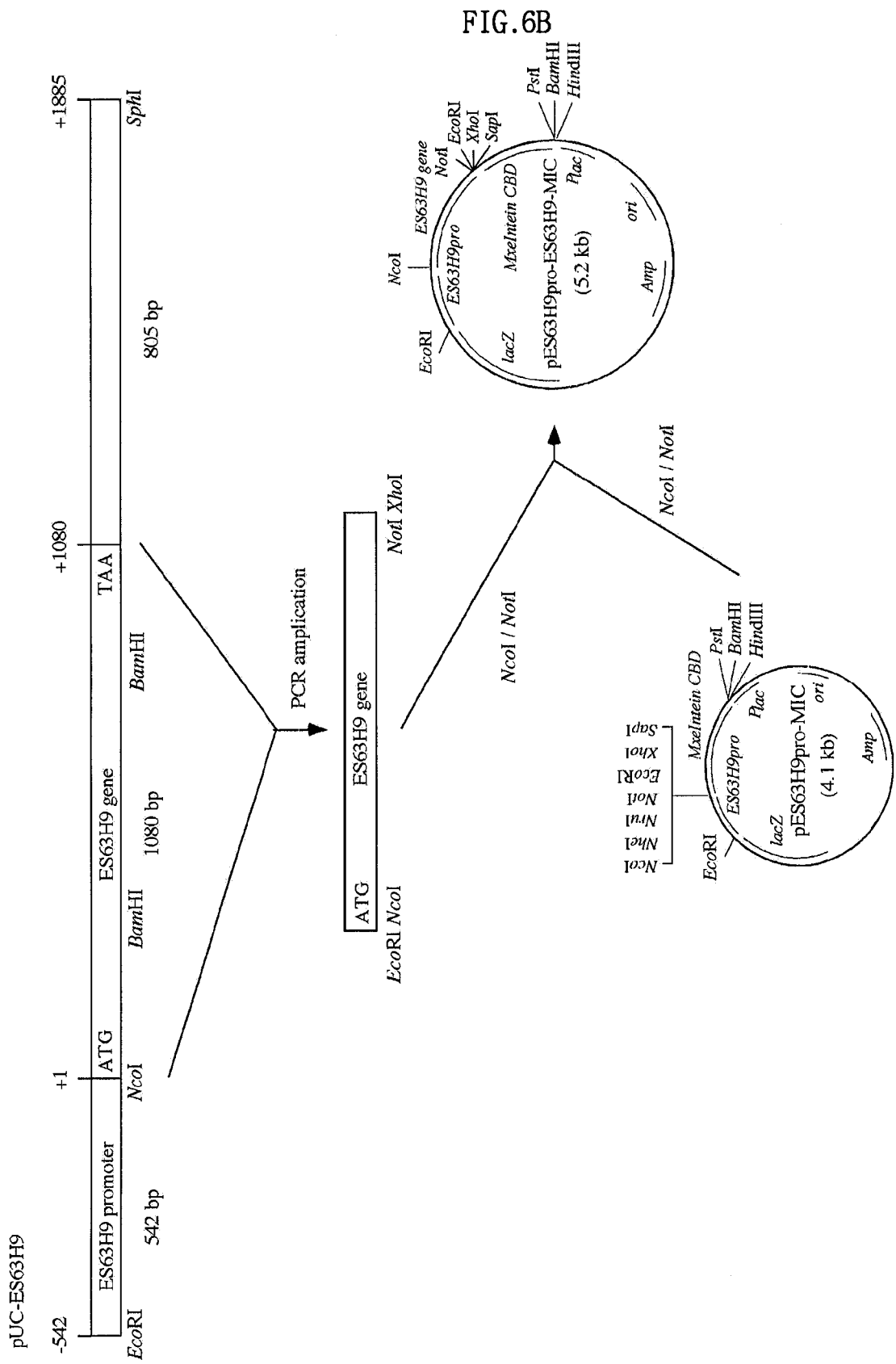

The preparation and cleavage map of pES63H9pro3-ES63H9-MIC (5.2 kb) that included a coding sequence of the present protease and promoter are indicated in FIGS. 6A and 6B. The DNA fragment introduced into the pES63H9pro3-ES63H9-MIC vector is shown in SEQ ID NO:8, and included the protease coding sequence, its own promoter, and an 853 bp-sized MxeIntein chitin binding domain (CBD) that was derived from the intervening sequence located between NcoI and BamHI in pTXB3.

The *E. coli* DH5α cells harbouring pES63H9pro3-ES63H9-MIC were grown in 1 l of LB broth supplemented with 100 μg ampicillin/ml at 37° C. for 12 h. The cells were collected by centrifugation at 5,000×g for 5 min, and suspended in 30 ml of an ice-cold column buffer (20 mM Tris/HCl (pH 7.4), 0.5 M NaCl, 0.2% Triton X-100, 2 mM EDTA).

After cell disruption was performed by repeating the sonication for 30 seconds and no treatment for 30 seconds five times with a Labsonic L (B. Braun International GmbH, Germany) sonicator, the disrupted sample was centrifuged at 20,000×g for 20 min.

2-3: Purification of Recombinant Protein

The supernatant obtained by the centrifugation was purified. Specifically, the cell-free extract was put on a chitin bead column (20 ml set volume) (New England Biolabs Inc.) equilibrated with a column buffer. The column was washed with the same buffer, and equilibrated with a cleavage buffer (column buffer with 30 mM DTT), and then allowed to stand at 4° C. overnight.

The proteins were eluted with a column buffer to a total volume of 50 ml. The amount of protein was measured using a BCA protein assay reagent (Pierce Biotechnology, USA), with bovine serum albumin as the standard protein.

The recombinant protease was purified 6.3-fold after affinity chromatography, with a specific activity of 76,000 U/mg and a final yield of 4.4% (Table 1).

TABLE 1

Purification of metalloprotease from the transformant

| Purification step | Total protein (mg/l) | Total activity (U) | Specific activity (U/mg) | Yield (%) |
| --- | --- | --- | --- | --- |
| Cell-free extract | 138 | 76,000 | 551 | 100 |
| Affinity chromatography | 1 | 3,400 | 3,400 | 4 |

FIG. 2 shows SDS-PAGE of protease from *E. coli* DH5α cells harboring pES63H9pro3-ES63H9-MIC. As shown in FIG. 2, *E. coli* DH5α cells harboring pES63H9pro3-ES63H9-MIC produced a high amount of protease.

The SDS-PAGE was performed by the Laemmli method with an 11% polyacrylamide gel. Specifically, the enzyme solution was mixed with the sample buffer and boiled for 5 min before being placed on the gel. The gels were stained for protein with GelCode Blue Stain Reagent (Pierce, Rockford, USA).

In FIG. 2, lane M is size marker, lane C is cell-free extract, and lane P is purified enzyme. The arrow indicates the position of protease. The SDS-PAGE of the purified enzyme exhibited a single band with an apparent molecular mass of 39 kDa (FIG. 2). This value agreed with that estimated from the DNA sequence.

Example 3

Enzyme Assay 3-1: Enzyme Assay

Protease activity was determined by measuring the release of acid-soluble material from azocasein (Sigma, USA) (Windle, H. J. P. et al., *Infect. Immun.* Vol. 65, pp 3132-3137, 1997).

Specifically, all assays were conducted in a 50 mM Tris-HCl (pH 7.0) buffer. Enzyme samples (100 µl) obtained in Example 2 were added to 100 µl of 1% (w/v) azocasein and the reaction mixture was incubated at 50° C. for 1 h and terminated by the addition of 400 µl of 10% (w/v) trichloroacetic acid. The precipitated protein was removed by centrifugation (12,000×g, 5 min), and the resulting supernatant was transferred to a clean tube containing 700 µl of 525 mM NaOH. Absorbance was measured at 442 nm.

One unit of protease activity was defined as an amount required for producing enough acid-soluble material from azocasein to yield absorbance of 0.1 at 442 nm, following 1 h incubation at 50° C.

3-2: Effects of Temperature and pH on Enzyme Activity and Stability

Figure 3:
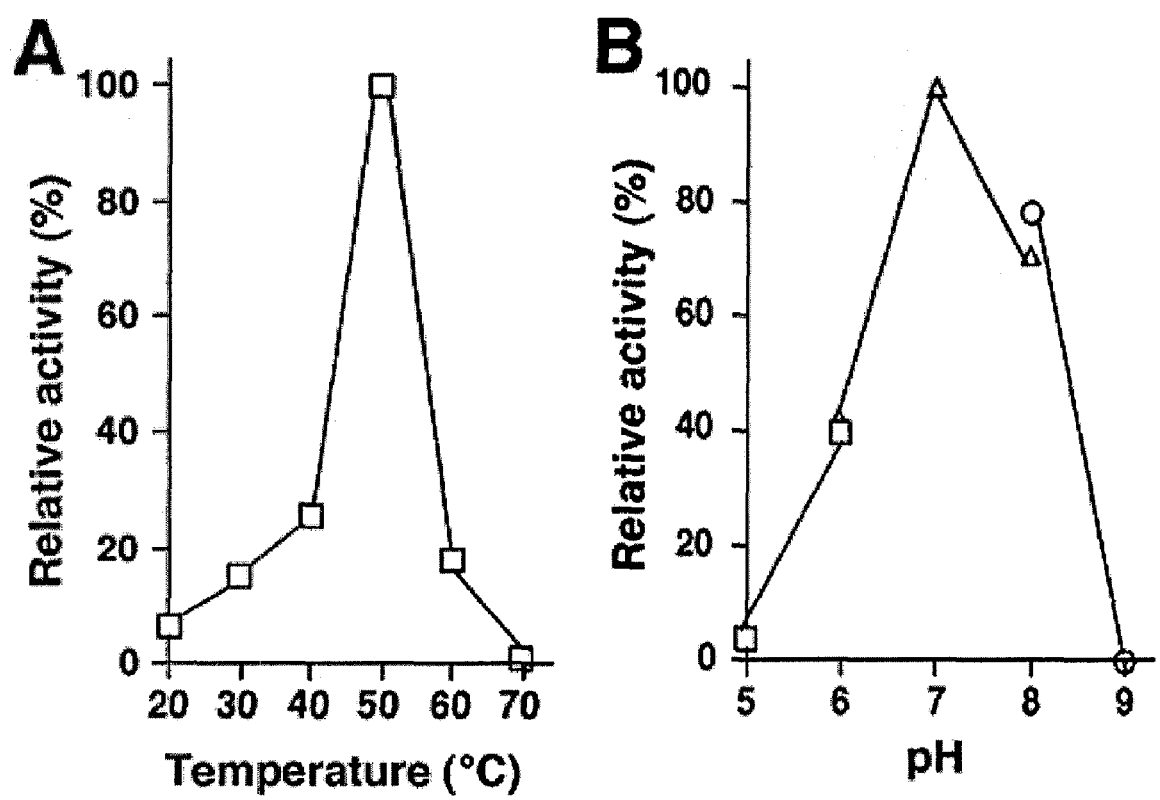
FIG. 3 is a graph showing the effects of temperature and pH on activity of recombinant metalloprotease according to the present invention.

The optimal temperature for protease activity was examined in the buffer used in the standard assay at various temperatures. The values on the ordinate are shown as percentages of the enzyme activity (100%) observed at 50° C. FIG. 3A shows the temperature dependence of the enzyme activity.

The optimal temperature for the activity of the protease was 50° C. for 1 h (FIG. 3A). Enzyme activity was 26% at 40° C. and 18% at 60° C., compared with the enzyme activity (100%) at 50° C. This result indicates that the enzyme showed its maximum activity at a narrow range of temperature.

The optimal pH for the protease activity was determined in various buffers at 50° C. The buffers used were sodium acetate buffers (open rectangles, pH 5.0-6.0), Tris-HCl buffers (open triangles, pH 6.0-8.0) and glycine-NaOH buffers (open circles, pH 8.0-9.0).

The values on the ordinate are shown as percentages of the enzyme activity (100%) observed at pH 7.0. FIG. 3B shows the pH dependence of the enzyme activity. The optimal pH for the activity of protease was 7.0 (FIG. 3B).

3-3: Effects of Metal Ions and Chemical Reagents on Enzyme Activity

The effects of various metal ions on activity of the enzyme according to the present invention were investigated using $CoCl_2$, $CaCl_2$, $MgCl_2$, $NiSO_4$, $CuSO_4$, $ZnSO_4$, and $FeSO_4$.

The effects of chemical reagents on activity of the enzyme according to the present invention were also assessed using ethylenediaminetetraacetic acid (EDTA), ethylene glycol-bis (2-aminoethylether)-N,N,N',N'-tetraacetic acid (EGTA), 1,10-phenantroline, sodium dodecyl sulfate (SDS), guanidine hydrochloride, and phenylmethylsulfonyl fluoride (PMSF). All these chemical reagents were purchased from Sigma (USA).

The purified enzymes were pre-incubated in the presence of metal ions or chemical reagents in a 50 mM Tris-HCl (pH 7.0) buffer at 25° C. for 30 min.

After 30 min of pre-incubation, residual protease activity was measured with 1% (W/V) azocasein.

As a control, the protease activity of the enzyme that was not pre-incubated with metal ions or chemical reagents was determined. The effects of various metal ions on the enzyme activity are summarized in Table 2.

TABLE 2

| Effect of metal ions and chemical reagents on enzyme activity (3,400 U/mg) | | |
|---|---|---|
| Metal ion or reagent | Concentration (mM) | Relative activity (%) |
| None | | 100 |
| $CoCl_2$ | 1 | 280 |
| $CaCl_2$ | 1 | 200 |
| $NiSO_4$ | 1 | 140 |
| $CuSO_4$ | 1 | 100 |
| $FeSO_4$ | 1 | 100 |
| $ZnCl_2$ | 1 | 80 |
| $MgCl_2$ | 1 | 20 |
| EDTA | 1 | 27 |
| EGTA | 1 | 21 |
| 1,10-phenanthroline | 1 | 55 |
| SDS | 17 | 9 |
| Guanidine hydrochloride | 500 | 22 |
| PMSF | 1 | 104 |

As shown in Table 2, the enzyme activities were enhanced by $Co^{2+}$, $Ca^{2+}$, and $Ni^{2+}$ ions, but inhibited by $Mg^{2+}$ and $Zn^{2+}$ ions. The enzyme activities were inhibited by 1 mM EDTA, EGTA, and 1,10-phenanthroline, well-known metalloprotease inhibitors. The enzyme was easily denatured by 0.05% SDS and strongly inhibited by 0.5 M guanidium hydrochloride, but PMSF, a serine protease inhibitor, had no influence.

Example 4

Fibrinolytic Assay

Fibrinolytic activity was determined using the method described by Datta et al. (Datta, et al., *Arch. Biochem. Biophys.* Vol. 317, pp 365-373, 1995) with minor modifications.

Figure 4:
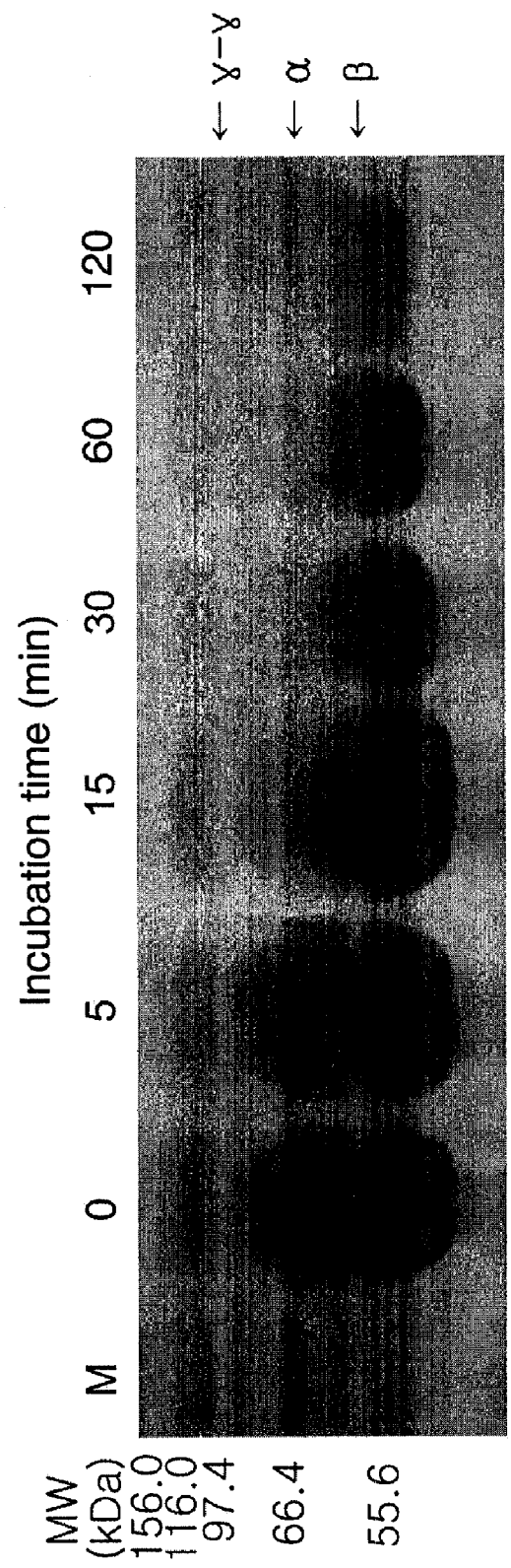
FIG. 4 is an SDS-PAGE gel photograph showing time-dependent hydrolysis of fibrin by recombinant metalloprotease according to the present invention.

Specifically, 10 µl of 1% human fibrinogen (Sigma, USA) solution (prepared in a 20 mM Tris/HCl (pH 7.4) buffer) was added to human thrombin (0.05 NIH unit, Sigma, USA), and then allowed to stand for 1 h at room temperature. Clots formed by the method were mixed with purified enzyme and incubated at 37° C. for up to 120 min. The hydrolysis of fibrin by the enzyme was analyzed by SDS-PAGE (FIG. 4). 5 µl each of reaction solutions was obtained at various time intervals and analyzed using an 11% SDS-PAGE gel. FIG. 4 shows time-dependent hydrolysis of fibrin by the metalloprotease.

As shown in FIG. 4, the purified enzyme completely hydrolyzed the α-chain and the γ-γ-chain at 37° C. after 1 h. The enzyme also partially hydrolyzed the β-chain after 30 min; however, it was not completely hydrolyzed after 2 h and even after 24 h (data not shown).

The present invention relates to a novel protease, a polynucleotide encoding the protease, and a fibrinolytic agent comprising the same. The protease is obtained from a new gene source by using metagenomic library technology, and can replace the conventional fibrinolytic agent.

What is claimed is:

1. An isolated Zn-dependent metalloprotease comprising the amino acid sequence shown in SEQ ID NO:2 and having fibrinolytic activity.

2. The Zn-dependent metalloprotease according to claim 1, wherein the metalloprotease is encoded by a polynucleotide comprising the nucleotide sequence shown in SEQ ID NO:1.

3. An isolated polynucleotide encoding a Zn-dependent metalloprotease comprising the amino acid sequence shown in SEQ ID NO:2.

4. The polynucleotide according to claim 3, wherein the polynucleotide comprises the nucleotide sequence shown in SEQ ID NO:1.

5. A vector comprising the polynucleotide encoding the Zn-dependent metalloprotease according to claim 3.

6. The vector according to claim 5, wherein the vector further comprises a promoter that has a size of 542 by to 546 by and comprises the nucleotide sequence shown in SEQ ID NO:3, wherein the promoter is connected to the 5' end of the polynucleotide encoding the Zn-dependent metalloprotease.

7. The vector according to claim 6, wherein the promoter has the nucleotide sequence shown in SEQ ID NO:4.

8. The vector according to claim 6, wherein the vector further comprises a nucleic acid sequence encoding an Mxe Intein chitin binding domain (CBD) fragment, wherein the Mxe Intein CBD-encodinq nucleic acid sequence is connected to the 3' end of the polynucleotide encoding the Zn-dependent metalloprotease and is prepared from the vector pTXB3 by cleaving with the restriction enzymes NcoI and BamHI.

9. The vector according to claim 8, wherein the vector comprises the polynucleotide having the nucleotide sequence shown in SEQ ID NO:5.

10. The vector according to claim 9, wherein the vector is pES63H9pro3-ES63H9-MIC as shown in FIG. 6a.

11. An expression vector comprising a promoter that has a size of 542 by to 546 by and that comprises the nucleotide sequence shown in SEQ ID NO:3, and that further comprises an Mxe Intein chitin binding domain (CBD) fragment that is prepared from the vector pTXB3 by cleaving with restriction enzymes NcoI and BamHI, wherein the expression vector is pES63H9pro3-MIC as shown in FIG. 5a.

12. A pharmaceutical composition comprising a Zn-dependent metalloprotease according to claim 1.

13. The pharmaceutical composition according to claim 12, wherein the composition is used as a fibrinolytic agent.

* * * * *

SEQUENCE LISTING

<160> NUMBER OF SEQ ID NOS: 13

<210> SEQ ID NO 1
<211> LENGTH: 1080
<212> TYPE: DNA
<213> ORGANISM: Artificial Sequence
<220> FEATURE:
<223> OTHER INFORMATION: Nucleic acid sequence for coding
      metalloprotease ES63H9 of the present invention
<220> FEATURE:
<221> NAME/KEY: CDS
<222> LOCATION: (1)..(1077)

<400> SEQUENCE: 1

```
atg gaa cca gaa ccg atc aaa acc tgc acc gtg ctc gag aat ccc ggc      48
Met Glu Pro Glu Pro Ile Lys Thr Cys Thr Val Leu Glu Asn Pro Gly
1               5                   10                  15 tat cag cct ata cac gca ccg aca gat gtt tca ccc caa cct gtg ctt      96
Tyr Gln Pro Ile His Ala Pro Thr Asp Val Ser Pro Gln Pro Val Leu
            20                  25                  30 gcg gcg atg gaa gca gtc ccc gtg cca aca ccg ccg cca act gtc gat     144
Ala Ala Met Glu Ala Val Pro Val Pro Thr Pro Pro Pro Thr Val Asp
        35                  40                  45 gcg gtc atg ctc ttc cgc aag aag tgg cgc gat ggc aag ata ctg cgt     192
Ala Val Met Leu Phe Arg Lys Lys Trp Arg Asp Gly Lys Ile Leu Arg
    50                  55                  60 gtc cac ttt atg gac ggc gac ccg gat gtg cac cgc aaa gtg gag gaa     240
Val His Phe Met Asp Gly Asp Pro Asp Val His Arg Lys Val Glu Glu
65                  70                  75                  80 gtg gct cac acc tgg agc cgc cat gcc aat gtt cgc ttc aag ttc gtc     288
Val Ala His Thr Trp Ser Arg His Ala Asn Val Arg Phe Lys Phe Val
                85                  90                  95 gac gat cca gcg gcg gat atc cgc att tcg ttt acg caa ccg gga tcc     336
Asp Asp Pro Ala Ala Asp Ile Arg Ile Ser Phe Thr Gln Pro Gly Ser
            100                 105                 110 tgg tct tat ctg gga acg gat gcg ctt cgg att gcc agg tcc caa tcg     384
Trp Ser Tyr Leu Gly Thr Asp Ala Leu Arg Ile Ala Arg Ser Gln Ser
        115                 120                 125 acg atg aat ttt ggc tgg ttg acg ccg cgc tct cca gac agc gag tat     432
Thr Met Asn Phe Gly Trp Leu Thr Pro Arg Ser Pro Asp Ser Glu Tyr
    130                 135                 140 aac cga gtg gtt att cac gaa ttt ggg cac gcg ctc ggc ctt gtg cat     480
Asn Arg Val Val Ile His Glu Phe Gly His Ala Leu Gly Leu Val His
145                 150                 155                 160 gaa cat caa aat ccc gac aac ggc att ccg tgg aac aaa ccg gcg gtc     528
Glu His Gln Asn Pro Asp Asn Gly Ile Pro Trp Asn Lys Pro Ala Val
                165                 170                 175 tac gaa tat tat agt ggc ccg ccc aac aac tgg tcc aaa gaa cag gtt     576
Tyr Glu Tyr Tyr Ser Gly Pro Pro Asn Asn Trp Ser Lys Glu Gln Val
            180                 185                 190 gac acc aat ctg ttc caa caa tat tca gaa gac cag gtc cgt ttc acc     624
Asp Thr Asn Leu Phe Gln Gln Tyr Ser Glu Asp Gln Val Arg Phe Thr
        195                 200                 205 ggc ttc gat cgc gaa tca atc atg ctc tac cca atc ccg aat gag ttc     672
Gly Phe Asp Arg Glu Ser Ile Met Leu Tyr Pro Ile Pro Asn Glu Phe
    210                 215                 220 act gta ggt gat ttc gaa gtt ggt tgg aac aga gat ctc tcg gct gat     720
Thr Val Gly Asp Phe Glu Val Gly Trp Asn Arg Asp Leu Ser Ala Asp
225                 230                 235                 240 gac aag gag ttc att ggc cgg atg tac ccc aag ccg gcc aac gag ttg     768
Asp Lys Glu Phe Ile Gly Arg Met Tyr Pro Lys Pro Ala Asn Glu Leu
```

```
                Asp Lys Glu Phe Ile Gly Arg Met Tyr Pro Lys Pro Ala Asn Glu Leu
                                245                 250                 255 atc gtc gat gat cca ccc cgc gcg tcc gaa atc agc aga tat ggc gaa        816
Ile Val Asp Asp Pro Pro Arg Ala Ser Glu Ile Ser Arg Tyr Gly Glu
            260                 265                 270 atc gac acc tat aca ttt ctg gtc acc caa aaa gga tcc tac cgc att        864
Ile Asp Thr Tyr Thr Phe Leu Val Thr Gln Lys Gly Ser Tyr Arg Ile
            275                 280                 285 gaa acc gac ggc cgg acg gac ctg gtg atg ctg cta tac ggg ccg gaa        912
Glu Thr Asp Gly Arg Thr Asp Leu Val Met Leu Leu Tyr Gly Pro Glu
            290                 295                 300 gat gac acc aaa ctg atc gcc gcc gat gat gat agt ggt cgc cgt ctg        960
Asp Asp Thr Lys Leu Ile Ala Ala Asp Asp Asp Ser Gly Arg Arg Leu
305                 310                 315                 320 aac ccg cgt atc act gaa gaa ctg gat tgg ggc aaa tac acg gtg cgt       1008
Asn Pro Arg Ile Thr Glu Glu Leu Asp Trp Gly Lys Tyr Thr Val Arg
                325                 330                 335 ttg cag cat ttc agc caa cgc cag acc ggt aaa tac gcc gtt ggc gtc       1056
Leu Gln His Phe Ser Gln Arg Gln Thr Gly Lys Tyr Ala Val Gly Val
                340                 345                 350 tat agg gat gac gcg gcg gag taa                                        1080
Tyr Arg Asp Asp Ala Ala Glu
            355

<210> SEQ ID NO 2
<211> LENGTH: 359
<212> TYPE: PRT
<213> ORGANISM: Artificial Sequence
<220> FEATURE:
<223> OTHER INFORMATION: Protein sequence of coding metalloprotease
      ES6349

<400> SEQUENCE: 2

Met Glu Pro Glu Pro Ile Lys Thr Cys Thr Val Leu Glu Asn Pro Gly
1               5                   10                  15

Tyr Gln Pro Ile His Ala Pro Thr Asp Val Ser Pro Gln Pro Val Leu
            20                  25                  30

Ala Ala Met Glu Ala Val Pro Pro Thr Pro Pro Thr Val Asp
        35                  40                  45

Ala Val Met Leu Phe Arg Lys Lys Trp Arg Asp Gly Lys Ile Leu Arg
    50                  55                  60

Val His Phe Met Asp Gly Asp Pro Asp Val His Arg Lys Val Glu Glu
65                  70                  75                  80

Val Ala His Thr Trp Ser Arg His Ala Asn Val Arg Phe Lys Phe Val
                85                  90                  95

Asp Asp Pro Ala Ala Asp Ile Arg Ile Ser Phe Thr Gln Pro Gly Ser
            100                 105                 110

Trp Ser Tyr Leu Gly Thr Asp Ala Leu Arg Ile Ala Arg Ser Gln Ser
        115                 120                 125

Thr Met Asn Phe Gly Trp Leu Thr Pro Arg Ser Pro Asp Ser Glu Tyr
    130                 135                 140

Asn Arg Val Val Ile His Glu Phe Gly His Ala Leu Gly Leu Val His
145                 150                 155                 160

Glu His Gln Asn Pro Asp Asn Gly Ile Pro Trp Asn Lys Pro Ala Val
                165                 170                 175

Tyr Glu Tyr Tyr Ser Gly Pro Pro Asn Asn Trp Ser Lys Glu Gln Val
            180                 185                 190

Asp Thr Asn Leu Phe Gln Gln Tyr Ser Glu Asp Gln Val Arg Phe Thr
```

```
             195                 200                 205
Gly Phe Asp Arg Glu Ser Ile Met Leu Tyr Pro Ile Pro Asn Glu Phe
    210                 215                 220

Thr Val Gly Asp Phe Glu Val Gly Trp Asn Arg Asp Leu Ser Ala Asp
225                 230                 235                 240

Asp Lys Glu Phe Ile Gly Arg Met Tyr Pro Lys Pro Ala Asn Glu Leu
                245                 250                 255

Ile Val Asp Asp Pro Pro Arg Ala Ser Glu Ile Ser Arg Tyr Gly Glu
            260                 265                 270

Ile Asp Thr Tyr Thr Phe Leu Val Thr Gln Lys Gly Ser Tyr Arg Ile
        275                 280                 285

Glu Thr Asp Gly Arg Thr Asp Leu Val Met Leu Leu Tyr Gly Pro Glu
    290                 295                 300

Asp Asp Thr Lys Leu Ile Ala Ala Asp Asp Ser Gly Arg Arg Leu
305                 310                 315                 320

Asn Pro Arg Ile Thr Glu Glu Leu Asp Trp Gly Lys Tyr Thr Val Arg
                325                 330                 335

Leu Gln His Phe Ser Gln Arg Gln Thr Gly Lys Tyr Ala Val Gly Val
            340                 345                 350

Tyr Arg Asp Asp Ala Ala Glu
        355

<210> SEQ ID NO 3
<211> LENGTH: 542
<212> TYPE: DNA
<213> ORGANISM: Artificial Sequence
<220> FEATURE:
<223> OTHER INFORMATION: Promoter sequence of metalloprotease ES63H9

<400> SEQUENCE: 3
gaattcaggg ctgtccgaac gccgctctgg ctgctcggtc tccggtgacg gcgcctgaga      60
gggcgcgctg gtgcgctctt ccgggattgc ctcctgcgcc gattcttcct tctgttcgcg     120
gctacgggag aagccctttg caattctat tccgccgctc tgctgcggat tgtcctcctg      180
gcccggcaaa atgattccac tcatgtgaac atcttctttc ttttcaacgt tttatcaagt     240
gagcaaatag taatttaaat acagtttaac cgaaccattg taccgtaaaa cggtggacct     300
caaaattatt acccatccac aactgcaata tctttcgttt gccagaatgg agggttaatt     360
cggcattgac cttactgtta acctgcggtt ataactttgt tgactttcgt gacgtctatg     420
caatcaccgt ccgtagtaag cgttgtaccc gcccgcctgc aatagcgcta aagcgcagac     480
cacggacggt attgttgtcg aagcccaagt gaaccactac tttggatcgc aaaggagaaa     540
cc                                                                    542

<210> SEQ ID NO 4
<211> LENGTH: 546
<212> TYPE: DNA
<213> ORGANISM: Artificial Sequence
<220> FEATURE:
<223> OTHER INFORMATION: Promoter sequence of metalloprotease ES63H9 for
      a expression vector

<400> SEQUENCE: 4
gaattcaggg ctgtccgaac gccgctctgg ctgctcggtc tccggtgacg gcgcctgaga      60
gggcgcgctg gtgcgctctt ccgggattgc ctcctgcgcc gattcttcct tctgttcgcg     120
gctacgggag aagccctttg caattctat tccgccgctc tgctgcggat tgtcctcctg      180
```

| | |
|---|---|
| gcccggcaaa atgattccac tcatgtgaac atcttctttc ttttcaacgt tttatcaagt | 240 |
| gagcaaatag taatttaaat acagtttaac cgaaccattg taccgtaaaa cggtggacct | 300 |
| caaaattatt acccatccac aactgcaata tctttcgttt gccagaatgg agggttaatt | 360 |
| cggcattgac cttactgtta acctgcggtt ataactttgt tgactttcgt gacgtctatg | 420 |
| caatcaccgt ccgtagtaag cgttgtaccc gcccgcctgc aatagcgcta aagcgcagac | 480 |
| cacggacggt attgttgtcg aagcccaagt gaaccactac tttggatcgc aaaggagaaa | 540 |
| ccatgg | 546 |

<210> SEQ ID NO 5
<211> LENGTH: 2427
<212> TYPE: DNA
<213> ORGANISM: Artificial Sequence
<220> FEATURE:
<223> OTHER INFORMATION: metalloprotease ES63-H9 related nucleic acid
  sequence which is incorporated in pUC-ES63H9

<400> SEQUENCE: 5

| | |
|---|---|
| gaattcaggg ctgtccgaac gccgctctgg ctgctcggtc tccggtgacg gcgcctgaga | 60 |
| gggcgcgctg gtgcgctctt ccgggattgc ctcctgcgcc gattcttcct tctgttcgcg | 120 |
| gctacgggag aagccctttg gcaattctat tccgccgctc tgctgcggat tgtcctcctg | 180 |
| gcccggcaaa atgattccac tcatgtgaac atcttctttc ttttcaacgt tttatcaagt | 240 |
| gagcaaatag taatttaaat acagtttaac cgaaccattg taccgtaaaa cggtggacct | 300 |
| caaaattatt acccatccac aactgcaata tctttcgttt gccagaatgg agggttaatt | 360 |
| cggcattgac cttactgtta acctgcggtt ataactttgt tgactttcgt gacgtctatg | 420 |
| caatcaccgt ccgtagtaag cgttgtaccc gcccgcctgc aatagcgcta aagcgcagac | 480 |
| cacggacggt attgttgtcg aagcccaagt gaaccactac tttggatcgc aaaggagaaa | 540 |
| ccatggaacc agaaccgatc aaaacctgca ccgtgctcga aatcccggc tatcagccta | 600 |
| tacacgcacc gacagatgtt tcaccccaac ctgtgcttgc ggcgatggaa gcagtccccg | 660 |
| tgccaacacc gccgccaact gtcgatgcgg tcatgctctt ccgcaagaag tggcgcgatg | 720 |
| gcaagatact gcgtgtccac tttatggacg gcgacccgga tgtgcaccgc aaagtggagg | 780 |
| aagtggctca cacctggagc cgccatgcca atgttcgctt caagttcgtc gacgatccag | 840 |
| cggcggatat ccgcatttcg tttacgcaac cgggatcctg gtcttatctg ggaacggatg | 900 |
| cgcttcggat tgccaggtcc aatcgacga tgaattttgg ctggttgacg ccgcgctctc | 960 |
| cagacagcga gtataaccga gtggttattc acgaatttgg gcacgcgctc ggccttgtgc | 1020 |
| atgaacatca aaatcccgac aacggcattc cgtggaacaa accggcggtc tacgaatatt | 1080 |
| atagtggccc gccaacaac tggtccaaag aacaggttga caccaatctg ttccaacaat | 1140 |
| attcagaaga ccaggtccgt ttcaccggct tcgatcgcga atcaatcatg ctctacccaa | 1200 |
| tcccgaatga gttcactgta ggtgatttcg aagttggttg gaacagagat ctctcggctg | 1260 |
| atgacaagga gttcattggc cggatgtacc ccaagccggc caacgagttg atcgtcgatg | 1320 |
| atccaccccg cgcgtccgaa atcagcagat atggcgaaat cgacacctat acatttctgg | 1380 |
| tcacccaaaa aggatcctac cgcattgaaa ccgacggccg gacggacctg gtgatgctgc | 1440 |
| tatacgggcc ggaagatgac accaaactga tcgccgccga tgatgatagt ggtcgccgtc | 1500 |
| tgaacccgcg tatcactgaa gaactggatt ggggcaaata cacggtgcgt ttgcagcatt | 1560 |
| tcagccaacg ccagaccggt aaatacgccg ttggcgtcta tgggatgac gcggcggagt | 1620 |

```
aaggcgctcc cagaatagaa agtcaccgat caactcccg ggcacaggcc acaggttacg    1680
ccattgagta gggcgccttt gacccatgcc ggggagttca attccggggg cggccttaca    1740
gcaaatcgca tgatacaatg taacccttga ccacaaagtg catccaacct gtatgaaatc    1800
atgttcgcaa cggtatgcag accagggttg aggaaatgat cgaaaacata tttaaggctt    1860
cggtaaacac tacatccacc accacttcca ttaccgcgtt ctcccgcgat cgcggcgcgt    1920
cgagtcatgg tctactttg aaattggcga ttatcctggg cgcgctcagt ctattgcttt    1980
tccttttcgg ggcatgtgga ggttcttctg cagccgcgcc aagcggtgaa gcgattgcct    2040
ttgaagagat gcccgaaggc atgggccgcg gctaccccaa cgtttcattg gccaatatca    2100
ataacaacgg cactggcctt gagaacggag atcgggctcc tggcttcaac ctgcagttgg    2160
aggatggcgc ctacattaat ctcgacgacc tgaaggtcg gccggttatg ctcaatttct    2220
gggcaacgtg gtgtccgccc tgccgggaag aaatgcccga cattatcaaa gcctatgaag    2280
cggacgatga gttggtggtg ctggccgtta acgtgcgcga agagatcggc gcggtgaatc    2340
cgtttacaga agatttccag atttccatgc cggtgttgct ggacccaaac gctgagctgt    2400
ccgagctctt cggcgtgctt ggcatgc                                        2427

<210> SEQ ID NO 6
<211> LENGTH: 25
<212> TYPE: DNA
<213> ORGANISM: Artificial Sequence
<220> FEATURE:
<223> OTHER INFORMATION: ES63H9_E2-F : Forward primer for amplifying
      ES63H9

<400> SEQUENCE: 6
gaattccatg gaaccagaac cgatc                                          25

<210> SEQ ID NO 7
<211> LENGTH: 31
<212> TYPE: DNA
<213> ORGANISM: Artificial Sequence
<220> FEATURE:
<223> OTHER INFORMATION: ES63H9_E1-R : Reverse primer for amplifying
      ES63H9_E1-R

<400> SEQUENCE: 7
gcggccgcgc tccgccgcgt catccctata g                                   31

<210> SEQ ID NO 8
<211> LENGTH: 2449
<212> TYPE: DNA
<213> ORGANISM: Artificial Sequence
<220> FEATURE:
<223> OTHER INFORMATION: Metalloprotease-related DNA sequence
      incorporated in pES63H9pro-ES63H9-MIC

<400> SEQUENCE: 8
gaattcaggg ctgtccgaac gccgctctgg ctgctcggtc tccggtgacg gcgcctgaga    60
gggcgcgctg gtgcgctctt ccgggattgc ctcctgcgcc gattcttcct tctgttcgcg    120
gctacgggag aagcccttg gcaattctat tccgccgctc tgctgcggat tgtcctcctg    180
gcccggcaaa atgattccac tcatgtgaac atcttcttc ttttcaacgt tttatcaagt    240
gagcaaatag taatttaaat acagtttaac cgaaccattg taccgtaaaa cggtggacct    300
caaaattatt acccatccac aactgcaata tctttcgttt gccagaatgg agggttaatt    360
cggcattgac cttactgtta acctgcggtt ataactttgt tgactttcgt gacgtctatg    420
```

```
caatcaccgt ccgtagtaag cgttgtaccc gcccgcctgc aatagcgcta aagcgcagac      480
cacggacggt attgttgtcg aagcccaagt gaaccactac tttggatcgc aaaggagaaa      540
ccatggaacc agaaccgatc aaaacctgca ccgtgctcga gaatcccggc tatcagccta      600
tacacgcacc gacagatgtt tcaccccaac ctgtgcttgc ggcgatggaa gcagtccccg      660
tgccaacacc gccgccaact gtcgatgcgg tcatgctctt ccgcaagaag tggcgcgatg      720
gcaagatact gcgtgtccac tttatggacg cgacccgga tgtgcaccgc aaagtggagg      780
aagtggctca cacctggagc cgccatgcca atgttcgctt caagttcgtc gacgatccag      840
cggcggatat ccgcatttcg tttacgcaac cgggatcctg gtcttatctg ggaacggatg      900
cgcttcggat tgccaggtcc aatcgacga tgaattttgg ctggttgacg ccgcgctctc      960
cagacagcga gtataaccga gtggttattc acgaatttgg gcacgcgctc ggccttgtgc     1020
atgaacatca aaatcccgac aacggcattc cgtggaacaa accggcggtc tacgaatatt     1080
atagtggccc gccaacaac tggtccaaag aacaggttga caccaatctg ttccaacaat     1140
attcagaaga ccaggtccgt ttcaccggct tcgatcgcga atcaatcatg ctctacccaa     1200
tcccgaatga gttcactgta ggtgatttcg aagttggttg gaacagagat ctctcggctg     1260
atgacaagga gttcattggc cggatgtacc ccaagccggc caacgagttg atcgtcgatg     1320
atccaccccg cgcgtccgaa atcagcagat atggcgaaat cgacacctat acatttctgg     1380
tcacccaaaa aggatcctac cgcattgaaa ccgacggccg gacggacctg gtgatgctgc     1440
tatacgggcc ggaagatgac accaaactga tcgccgccga tgatgatagt ggtcgccgtc     1500
tgaacccgcg tatcactgaa gaactggatt ggggcaaata cacggtgcgt ttgcagcatt     1560
tcagccaacg ccagaccggt aaatacgccg ttggcgtcta tagggatgac gcggcggagc     1620
gcggccgcga attcctcgag ggctcttcct gcatcacggg agatgcacta gttgccctac     1680
ccgagggcga gtcggtacgc atcgccgaca tcgtgccggg tgcgcggccc aacagtgaca     1740
acgccatcga cctgaaagtc cttgaccggc atggcaatcc cgtgctcgcc gaccggctgt     1800
tccactccgg cgagcatccg gtgtacacgg tgcgtacggt cgaaggtctg cgtgtgacgg     1860
gcaccgcgaa ccacccgttg ttgtgtttgg tcgacgtcgc cggggtgccg accctgctgt     1920
ggaagctgat cgacgaaatc aagccgggcg attacgcggt gattcaacgc agcgcattca     1980
gcgtcgactg tgcaggtttt gcccgcggaa aacccgaatt tgcgcccaca acctacacag     2040
tcggcgtccc tggactggtg cgtttcttgg aagcacacca ccgagacccg gacgcccaag     2100
ctatcgccga cgagctgacc gacgggcggt tctactacgg gaaagtcgcc agtgtcaccg     2160
acgccggcgt gcagccggtg tatagccttc gtgtcgacac ggcagaccac gcgtttatca     2220 cgaacggggtt cgtcagccac gctactggcc tcaccggtct gaactcaggc ctcacgacaa     2280
atcctggtgt atccgcttgg caggtcaaca cagcttatac tgcgggacaa ttggtcacat     2340 ataacgcaa gacgtataaa tgtttgcagc cccacacctc cttggcagga tgggaaccat     2400
ccaacgttcc tgccttgtgg cagcttcaat gactgcagga aggggatcc                 2449
```

<210> SEQ ID NO 9
<211> LENGTH: 853
<212> TYPE: DNA
<213> ORGANISM: Artificial Sequence
<220> FEATURE:
<223> OTHER INFORMATION: Mxe Intein chiten binding domain (CBD)

<400> SEQUENCE: 9

```
ccatggctag ctcgcgagtc gacggcggcc gcgaattcct cgagggctct tcctgcatca        60
```

-continued

```
cgggagatgc actagttgcc ctacccgagg gcgagtcggt acgcatcgcc gacatcgtgc    120
cgggtgcgcg gcccaacagt gacaacgcca tcgacctgaa agtccttgac cggcatggca    180
atcccgtgct cgccgaccgg ctgttccact ccggcgagca tccggtgtac acggtgcgta    240
cggtcgaagg tctgcgtgtg acgggcaccg cgaaccaccc gttgttgtgt ttggtcgacg    300
tcgccggggt gccgaccctg ctgtggaagc tgatcgacga aatcaagccg gcgattacg     360 cggtgattca acgcagcgca ttcagcgtcg actgtgcagg ttttgcccgc ggaaaacccg    420
aatttgcgcc cacaacctac acagtcggcg tccctggact ggtgcgtttc ttggaagcac    480
accaccgaga cccggacgcc caagctatcg ccgacgagct gaccgacggg cggttctact    540
acgcgaaagt cgccagtgtc accgacgccg gcgtgcagcc ggtgtatagc cttcgtgtcg    600
acacggcaga ccacgcgttt atcacgaacg ggttcgtcag ccacgctact ggcctcaccg    660
gtctgaactc aggcctcacg acaaatcctg gtgtatccgc ttggcaggtc aacacagctt    720
atactgcggg acaattggtc acatataacg gcaagacgta taaatgtttg cagccccaca    780
cctccttggc aggatgggaa ccatccaacg ttcctgcctt gtggcagctt caatgactgc    840
aggaagggga tcc                                                       853
```

<210> SEQ ID NO 10
<211> LENGTH: 5
<212> TYPE: PRT
<213> ORGANISM: Artificial Sequence
<220> FEATURE:
<223> OTHER INFORMATION: Conserved amino acid sequence in an active site of the metalloprotease, activity is inhibited by a metal chelating agents Mg2+ or ZN2+.

<400> SEQUENCE: 10

His Glu Phe Gly His
1               5

<210> SEQ ID NO 11
<211> LENGTH: 5
<212> TYPE: PRT
<213> ORGANISM: Artificial Sequence
<220> FEATURE:
<223> OTHER INFORMATION: Conserved amino acid sequence in an active site of the metalloprotease.
<220> FEATURE:
<221> NAME/KEY: MISC_FEATURE
<222> LOCATION: (3)..(4)
<223> OTHER INFORMATION: X is non-conserved amino acid.

<400> SEQUENCE: 11

His Glu Xaa Xaa His
1               5

<210> SEQ ID NO 12
<211> LENGTH: 11
<212> TYPE: PRT
<213> ORGANISM: Artificial Sequence
<220> FEATURE:
<223> OTHER INFORMATION: Astacins, metalloprotease, and snake venom exhibited identical zinc-binding environments.
<220> FEATURE:
<221> NAME/KEY: MISC_FEATURE
<222> LOCATION: (3)..(10)
<223> OTHER INFORMATION: X is non-conserved amino acid.

<400> SEQUENCE: 12

His Glu Xaa Xaa His Xaa Xaa Gly Xaa Xaa His
1               5                   10

```
<210> SEQ ID NO 13
<211> LENGTH: 12
<212> TYPE: PRT
<213> ORGANISM: Artificial Sequence
<220> FEATURE:
<223> OTHER INFORMATION: Conserved sequence in zinc-dependent
      metallopeptidase family members (accession no. CDD16541).
<220> FEATURE:
<221> NAME/KEY: MISC_FEATURE
<222> LOCATION: (3)..(10)
<223> OTHER INFORMATION: X is non-conversed amino acid.

<400> SEQUENCE: 13

His Glu Xaa Xaa His Ala Leu Gly Xaa Xaa His Glu
1               5                   10
```